(12) United States Patent
Oh et al.

(10) Patent No.: US 10,413,253 B2
(45) Date of Patent: Sep. 17, 2019

(54) METHOD AND APPARATUS FOR PROCESSING MEDICAL IMAGE

(71) Applicant: Samsung Electronics Co., Ltd., Suwon-si (KR)

(72) Inventors: Ji-hun Oh, Hwaseong-si (KR); Gye-hyun Kim, Seoul (KR); Jae-sung Lee, Seoul (KR); Min-su Cheon, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 384 days.

(21) Appl. No.: 14/949,676

(22) Filed: Nov. 23, 2015

(65) Prior Publication Data
US 2016/0148375 A1    May 26, 2016

(30) Foreign Application Priority Data

Nov. 21, 2014 (KR) .................. 10-2014-0163823
Oct. 5, 2015 (KR) .................. 10-2015-0139997

(51) Int. Cl.
*G06K 9/00* (2006.01)
*A61B 5/00* (2006.01)
(Continued)

(52) U.S. Cl.
CPC .............. *A61B 5/743* (2013.01); *A61B 5/055* (2013.01); *A61B 5/4504* (2013.01); *A61B 5/7264* (2013.01); *A61B 5/7275* (2013.01); *A61B 6/032* (2013.01); *A61B 6/505* (2013.01); *A61B 6/5217* (2013.01); *G06T 11/008* (2013.01); *A61B 6/4291* (2013.01); *A61B 6/461* (2013.01); *A61B 6/467* (2013.01); *A61B 6/563* (2013.01); *A61B 2576/00* (2013.01); *G16H 50/30* (2018.01); *H04N 5/202* (2013.01)

(58) Field of Classification Search
None
See application file for complete search history.

(56) References Cited

U.S. PATENT DOCUMENTS 5,991,028 A * 11/1999 Cabib .................. C12Q 1/6816
356/456
8,634,626 B2    1/2014 Shi et al.
(Continued)

FOREIGN PATENT DOCUMENTS

DE    102013220018 A1    4/2014
JP    2008217493 A    9/2008

OTHER PUBLICATIONS

Hamaoka, Tsuyoshi, et al. "Bone imaging in metastatic breast cancer." Journal of Clinical Oncology 22.14 (2004): 2942-2953.*
(Continued)

*Primary Examiner* — Sean M Conner
(74) *Attorney, Agent, or Firm* — Nixon & Vanderhye P.C.

(57) ABSTRACT

Provided is a medical image processing apparatus including: a data acquisition unit configured to respectively acquire a plurality of medical images representing an object including at least one target at a plurality of different time points; and an image processor configured to generate, based on the acquired plurality of medical images, a diagnostic image showing a degree of change that has occurred in the at least one target over the plurality of different time points.

19 Claims, 19 Drawing Sheets

(51) Int. Cl.
*A61B 5/055* (2006.01)
*A61B 6/03* (2006.01)
*A61B 6/00* (2006.01)
*G06T 11/00* (2006.01)
*H04N 5/202* (2006.01)
*G16H 50/30* (2018.01)

(56) References Cited

U.S. PATENT DOCUMENTS

| | | | | |
|---|---|---|---|---|
| 2005/0137159 | A1* | 6/2005 | Bab | A61K 31/00 514/44 R |
| 2007/0031018 | A1* | 2/2007 | Camus | A61B 6/481 382/130 |
| 2008/0049999 | A1 | 2/2008 | Jarebko et al. | |
| 2008/0242977 | A1 | 10/2008 | Sirohey et al. | |
| 2009/0092305 | A1* | 4/2009 | Ditt | A61B 5/7207 382/131 |
| 2010/0067767 | A1* | 3/2010 | Arakita | A61B 6/504 382/131 |
| 2010/0246925 | A1* | 9/2010 | Nagatsuka | A61B 5/08 382/132 |
| 2011/0130661 | A1 | 6/2011 | Lee et al. | |
| 2011/0268338 | A1 | 11/2011 | JCollins et al. | |
| 2011/0274330 | A1* | 11/2011 | Mori | G06T 7/0016 382/131 |
| 2013/0077845 | A1* | 3/2013 | Flohr | A61B 6/032 382/131 |
| 2014/0003700 | A1* | 1/2014 | Hermosillo Valadez | G06T 11/003 382/131 |
| 2014/0132597 | A1* | 5/2014 | Tsukagoshi | G06T 15/08 345/419 |
| 2014/0226889 | A1* | 8/2014 | Liu | G06T 7/174 382/131 |
| 2014/0296691 | A1* | 10/2014 | Kawasaki | A61B 5/14542 600/407 |
| 2015/0165235 | A1* | 6/2015 | Fujisawa | A61N 5/1037 382/131 |

OTHER PUBLICATIONS

Int'l Search Report and Written Opinion for PCT/KR2015/012580 dated Feb. 29, 2016.
Huang, S. F., and Chiang, K H., Automatic Detection of Bone Metastasis in Vertebrae by Using CT Images, Proceedings of the World Congress on Engineering 2012 vol. II, London.
O'Connor, S., et al., Lytic Metastases in Thoracolumbar Spine: Computer-Aided Detection at CT-Preliminary Study, Radiology, vol. 242, No. 3, Mar. 2007.
Wiese, T., et al., Computer-Aided Detection of Sclerotic Bone Metastases in the Spine Using Watershed Algorithm and Support Vector Machines, ISBI 2011.
Extended European Search Report Appln No. 15861181.4 dated Nov. 22, 2017.

\* cited by examiner

METHOD AND APPARATUS FOR PROCESSING MEDICAL IMAGE

RELATED APPLICATION(S)

This application claims the benefit of Korean Patent Application No. 10-2014-0163823, filed on Nov. 21, 2014, and Korean Patent Application No. 10-2015-0139997, filed on Oct. 5, 2015, in the Korean Intellectual Property Office, the disclosures of which are incorporated herein in their entireties by reference.

BACKGROUND

The present disclosure relates to a method and apparatus for processing a medical image, and more particularly, to a method and apparatus for processing a plurality of medical images to diagnose a patient's disease.

Medical imaging apparatuses are used to acquire images of internal organs and body parts. The medical imaging apparatuses are non-invasive examination apparatuses that can capture detailed images of structures, tissue, fluid flow, etc., inside a body and provide the images to a user. A user, for example, a medical practitioner, may use medical images from the medical imaging apparatuses to diagnose a patient's condition.

Examples of a medical imaging apparatus include a magnetic resonance imaging (MRI) apparatus, a computed tomography (CT) apparatus, an X-ray apparatus, an ultrasound diagnosis apparatus, and the like.

A CT apparatus is capable of providing a cross-sectional image of an object. Furthermore, the CT apparatus may represent an internal structure (e.g., organs such as kidney, lung, etc.) of the object without superimposition of other body parts in front of and/or behind the internal structure, unlike a traditional X-ray apparatus. Due to these advantages, the CT apparatus has been widely used for precise diagnosis of diseases.

A CT apparatus emits an X-ray towards an object, detects the X-ray that has passed through the object, and reconstructs an image by using the detected X-ray.

An MRI apparatus uses a magnetic field to capture an image of a subject, and is widely used to accurately diagnose diseases because it shows stereoscopic images of bones, lumbar discs, joints, nerve ligaments, etc., at desired angles. The MRI apparatus acquires MR signals by using a radio frequency (RF) multi-coil such as, for example, RF coils, a permanent magnet, gradient coils, etc. and samples the acquired MR signals, thereby reconstructing an MR image.

As described above, medical images obtained by various medical imaging apparatuses depict an object in various ways according to the type of medical imaging apparatus and scanning method used.

A doctor may analyze a medical image and determine the presence of disease or abnormal health conditions in a patient. Thus, a medical imaging apparatus that processes medical images to generate a diagnostic image so that a user, e.g., a medical practitioner, may assess or diagnose a patient's disease would be useful.

SUMMARY

Provided are methods and apparatuses for processing a medical image to facilitate observation or diagnosis of a patient's disease by a user. The user may easily determine or recognize a change in status of a patient's disease when the user needs to track and monitor the patient's disease at time intervals. The user may process a medical image to generate a diagnostic image so that the user may determine a degree of change with respect to, for example, metastatic bone cancer when follow-up monitoring of the metastatic bone cancer is needed.

Additional aspects will be set forth in the description that follows and/or learned by practice of the presented exemplary embodiments.

According to an aspect of an exemplary embodiment, a medical image processing apparatus includes: a data acquisition unit configured to acquire a plurality of medical images representing an object, including at least one target in the object, corresponding to a plurality of different time points, wherein at least one of the plurality of medical images correspond to one of the plurality of different time points; and an image processor configured to generate, based on the plurality of medical images, a diagnostic image showing at least one degree of change in at least one target over the plurality of different time points.

The image processor may classify each of the at least one degree of change into one of a plurality of stages and generate the diagnostic image showing at least one degree of change, and to distinguish each of the plurality of stages from others of the plurality of stages.

The image processor may register the plurality of medical images to generate a plurality of registered medical images, and to quantify each of the at least one degree of change into one of a plurality of stages based on a variation in pixel intensity between corresponding pixels in the plurality of registered medical images.

The image processor may classify each of the at least one degree of change into one of a plurality of stages, and to distinguish each of the plurality of stages in the diagnostic image by use of at least one of colors, shapes, marks, and lines. The medical image processing apparatus may further include a user interface unit configured to receive input to select colors, shapes, marks, and/or lines to distinguish the plurality of stages.

The image processor may classify each of the at least one degree of change into one of a plurality of stages, and use color to distinguish each of the plurality of stages in the diagnostic image from others of the plurality of stages. The medical image processing apparatus may further include a user interface unit configured to receive input to set different colors to the plurality of stages.

The image processor may classify the degree of change into a plurality of stages and generate the diagnostic image showing the degree of change in at least one target by using a plurality of different colors corresponding to the plurality of stages.

The medical image processing apparatus may further comprise a user interface unit configured to receive input to map each of the plurality of stages to a different color.

The at least one degree of change may comprise at least one of a physiological change, a position change, a size change, and a shape change.

The object may include a part of a patient's body, and at least one target may be a bone in the part of the patient's body.

The diagnostic image may be an image showing the degree of change in the bone that is classified into one of the plurality of stages and representing a degree of progression of metastatic bone cancer including at least one of lytic metastatic cancer and blastic metastatic cancer.

The diagnostic image may include a target-extracted image representing at least one target and showing at least one degree of change as one of a plurality of stages.

The diagnostic image may include an overlay image obtained by registering and superimposing a plurality of medical images and showing at least one degree of change as one of a plurality of stages.

The diagnostic image may be a blended image obtained by blending at least one of a plurality of medical images with an image showing at least one degree of change that has been classified into one of a plurality of stages.

The image processor may obtain a plurality of target-extracted images respectively corresponding to the plurality of different time points by extracting at least one target from each of the plurality of medical images, to generate a plurality of registered images by registering the plurality of target-extracted images, and to generate the diagnostic image based on the plurality of registered images.

The image processor may be configured to extract at least one target by segmenting at least one target from each of the plurality of medical images.

The image processor may generate the plurality of registered images by registering the plurality of target-extracted images using at least one of rigid registration and non-rigid registration.

The image processor may perform symmetric registration to reduce a quantification error caused by blurring that occurs during warping, by using at least one of the rigid registration and the non-rigid registration.

The image processor may calculate a variation of at least one target in the plurality of medical images based on the plurality of registered images, to quantify the calculated variation, and to classify at least one degree of change into one of a plurality of stages based on the quantified variation.

The image processor may quantify at least one degree of change based on a variation in pixel intensity between corresponding pixels in the plurality of registered images.

The image processor may map the plurality of stages to colors and indicate at least one degree of change in at least one target by using the mapped colors. The colors may be chromatic or achromatic.

The image processor may generate the diagnostic image by blending at least one of the plurality of medical images with an image showing at least one degree of change in at least one target using the mapped colors, using at least one of linear transformation, Gamma transformation, or contrast stretching transformation.

The image processor may filter the plurality of registered images to remove a false positive having a predetermined form and to generate a diagnostic image based on the filtered plurality of registered images.

The medical image processing apparatus may further include a display unit configured to display the diagnostic image.

The medical image processing apparatus may further include a display unit configured to display the diagnostic image and at least one of the plurality of medical images.

The medical image processing apparatus may further include a display unit configured to display the diagnostic image and a plurality of registered medical images obtained by registering the plurality of medical images.

The image processor may numerically calculate the at least one degree of change in the at least one target and to generate information indicating a result of the numerical calculation.

The medical image processing apparatus may further include a display unit configured to display the information and the diagnostic image.

The plurality of medical images may be a plurality of computed tomography (CT) images, and the image processor may be configured to perform iterative reconstruction or filtering in an image domain to correct inhomogeneity in image quality of the plurality of CT images.

The image processor may perform a partial volume correction method on at least one of the plurality of medical images and the diagnostic image.

According to an aspect of another exemplary embodiment, a medical image processing method includes: acquiring a plurality of medical images representing an object, including at least one target in the object, corresponding to a plurality of different time points, wherein at least one of the plurality of medical images correspond to one of the plurality of different time points; calculating, based on the plurality of medical images, at least one degree of change that has occurred in at least one target over the plurality of different time points; and generating a diagnostic image showing at least one degree of change in at least one target.

The generating of the diagnostic image may include: classifying each of the at least one degree of change into one of a plurality of stages, wherein each of the plurality of stages is distinguished from others of the plurality of stages; and showing on the diagnostic image at least one degree of change.

The generating of the diagnostic image may include: generating a plurality of registered medical images by registering the plurality of medical images; and quantifying each of the at least one degree of change into one of a plurality of stages based on a variation in pixel intensity between corresponding pixels in the plurality of registered medical images, wherein each of the plurality of stages is distinguished from others of the plurality of stages.

The generating of the diagnostic image may include classifying at least one degree of change into one of a plurality of stages and distinguishing each of the plurality of stages from others of the plurality of stages using at least one of colors, shapes, marks, and lines.

Input may be received to select at least one of colors, shapes, marks, and lines to distinguish the each of the plurality of stages.

The change may include at least one of a physiological change, a position change, a size change, and a shape change that have occurred in at least one target.

The generating of the diagnostic image may include: classifying each of the at least one degree of change into one of a plurality of stages; and showing the degree of change in at least one target by using color for each of the plurality of stages to distinguish each of the plurality of stages from others of the plurality of stages. Input may be received to map each of the plurality of stages to a different color.

The diagnostic image may include a target-extracted image, representing the at least one target, generated by extracting the at least one target from at least one of the plurality of medical images.

The diagnostic image may include an overlay image obtained by registering and superimposing the plurality of medical images.

The diagnostic image may be a blended image obtained by blending at least one of the plurality of medical images with an image showing at least one degree of change classified into one of a plurality of stages.

The generating of the diagnostic image may include: obtaining a plurality of target-extracted images respectively corresponding to the plurality of different time points by extracting at least one target from each of the plurality of medical images; generating a plurality of registered images by registering the plurality of target-extracted images; and generating the diagnostic image based on the plurality of registered images.

Obtaining the plurality of target-extracted images may include segmenting at least one target to extract the target.

Generating the plurality of registered images may include registering the plurality of target-extracted images by using at least one of rigid registration and non-rigid registration.

Generating the plurality of registered images may include performing symmetric registration to reduce a quantification error caused by blurring that occurs during warping, by using the at least one of the rigid registration and the non-rigid registration.

Generating the diagnostic image based on the plurality of registered images may further comprise calculating a variation of at least one target in the plurality of medical images based on the plurality of registered images, quantifying the variation, and classifying at least one degree of change into one of a plurality of stages based on the quantified variation.

Generating the diagnostic image based on the plurality of registered images may further include quantifying the variation in pixel intensity between corresponding pixels in the plurality of registered images.

Generating the diagnostic image based on the plurality of registered images may include filtering to remove a false positive having a predetermined form from among at least one target in the plurality of registered images.

The medical image processing method may further include displaying the diagnostic image.

The medical image processing method may further include: generating information indicating a result of calculating at least one degree of change; and displaying the information and the diagnostic image.

The plurality of medical images may be a plurality of CT images obtained by performing CT scans, and the medical image processing method may further include performing iterative reconstruction or filtering in an image domain to correct inhomogeneity in image quality of the plurality of CT images.

The medical image processing method may further include performing a partial volume correction method on at least one of the plurality of medical images and the diagnostic image.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
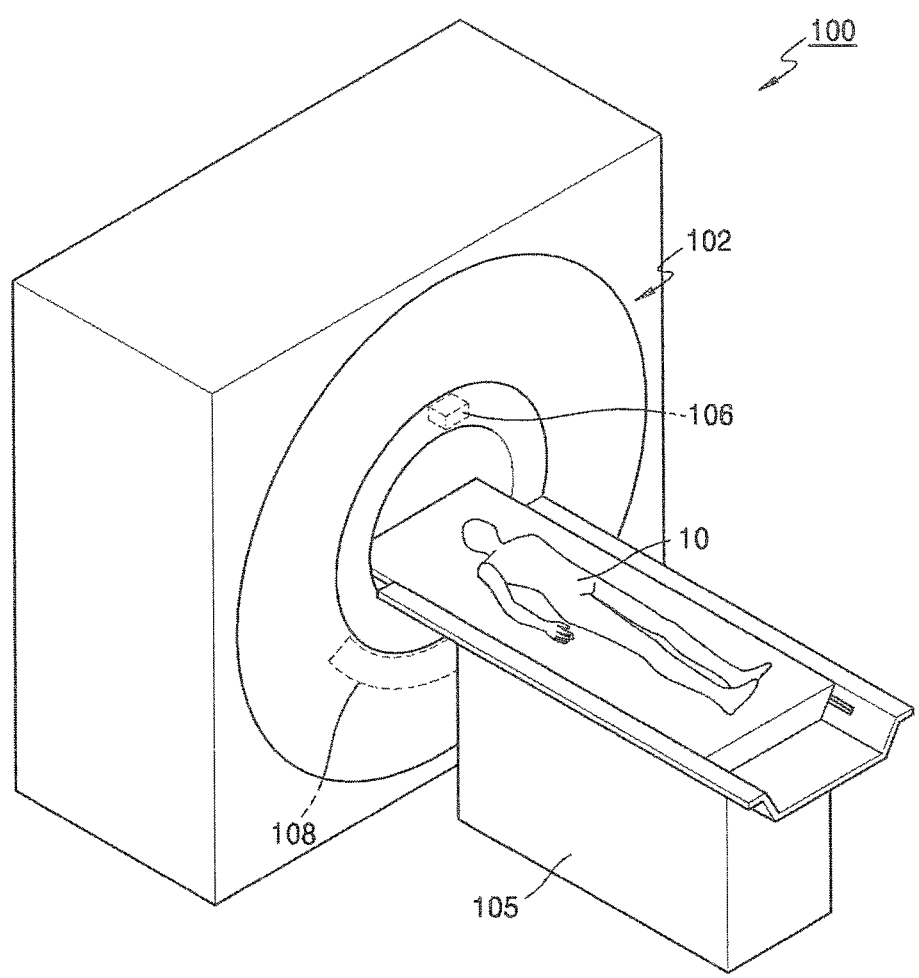
FIG. 1 is a schematic diagram of a computed tomography (CT) system.

Advantages and features of one or more embodiments of the present disclosure and methods of accomplishing the same may be understood more readily by reference to the following detailed description of the embodiments and the accompanying drawings.

In this regard, the present embodiments should not be construed as being limited to the descriptions set forth herein. Rather, these embodiments are provided as examples so that this disclosure will be thorough and complete and will fully convey the concept of the present embodiments to one of ordinary skill in the art. The appended claims illustrate some of the embodiments of the present disclosure.

Like reference numerals refer to like elements throughout the specification. All terms including descriptive or technical terms used herein should be construed as having meanings that are obvious to one of ordinary skill in the art. When a term has an ambiguous meaning due to evolving of language, precedent cases, or the appearance of new technologies, the meaning of a term used in this disclosure should first be clarified by its usage and/or definition in this disclosure. The term should then be clarified as one of ordinary skill in the art would have understood the term at the time of this disclosure.

When a part "includes" or "comprises" an element, unless there is a particular description contrary thereto, the part can further include other elements. The term "unit" in the embodiments of the present disclosure means a software component or a hardware component that performs a specific function. The hardware component may include, for example, a field-programmable gate array (FPGA) or an application-specific integrated circuit (ASIC).

Software component may refer to executable code and/or data used by the executable code in an addressable storage medium. Thus, software components may be, for example, object-oriented software components, class components, and task components, and may include processes, functions, attributes, procedures, subroutines, segments of program code, drivers, firmware, micro codes, circuits, data, a database, data structures, tables, arrays, or variables.

A function provided by a "unit" may be divided into additional components and "units."

Reference will now be made in detail to embodiments, examples of which are illustrated in the accompanying drawings. In this regard, the present embodiments may have different forms and should not be construed as being limited to the descriptions set forth herein.

In the following description, well-known functions or constructions are not described in detail so as not to obscure the embodiments with unnecessary detail.

In the present specification, an "image" may refer to multi-dimensional data composed of discrete image elements (e.g., pixels in a two-dimensional (2D) image and voxels in a three-dimensional (3D) image). For example, the image may include a medical image of an object captured by a computed tomography (CT) imaging apparatus. Throughout the specification, a "CT image" may mean an image generated by synthesizing a plurality of X-ray images obtained by a CT imaging apparatus that may rotate around at least one axis with respect to an object.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof.

Additionally, the object may be a "phantom" in this disclosure. A phantom is defined as a material having a density, an effective atomic number, and volume that are approximately the same as those of an organism. For example, the phantom may be a spherical shape having properties similar to the human body.

Furthermore, in the present specification, a "user" may be, but is not limited to, a medical expert, such as a medical doctor, a nurse, a medical laboratory technologist, or a technician who repairs a medical apparatus.

Since a CT system is capable of providing a cross-sectional image of an object, the CT system may distinctively express an inner structure of an object such as, for example, a kidney or a lung, compared to a traditional X-ray imaging apparatus. The CT system may obtain a plurality of image data for image slices of about 2 mm in thickness. The images may be created several tens to several hundred times per second and then may process the plurality of pieces of image data, so that the CT system may provide a relatively accurate image of the object.

Initially, only a horizontal cross-sectional image of the object could be obtained, but this issue has been overcome with various image reconstruction methods. Examples of 3D image reconstruction methods are:

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value from among voxels that construct an image.

Volume rendering (VR)—an imaging method capable of adjusting a color and transmittance of voxels that constitute an image, according to areas of interest.

Virtual endoscopy—a method that allows endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels so as to allow a user to easily observe an area of interest in volume rendering.

Voxel of interest (VOI)—a method of displaying only a selected area in volume rendering.

A CT system 100 according to an embodiment of the disclosure will now be described with reference to FIGS. 1 and 2.

FIG. 1 schematically illustrates the CT system 100. Referring to FIG. 1, the CT system 100 may include a gantry 102, a table 105, an X-ray generating unit 106, and an X-ray detecting unit 108. The gantry 102 may include the X-ray generating unit 106 and the X-ray detecting unit 108. An object 10 may be positioned on the table 105.

The table 105 may move in a predetermined direction (e.g., at least one of up, down, right, and left directions) during a CT imaging procedure. Also, the table 105 may be able to tilt or rotate. The gantry 102 may also be able to tilt in certain directions.

Figure 2:
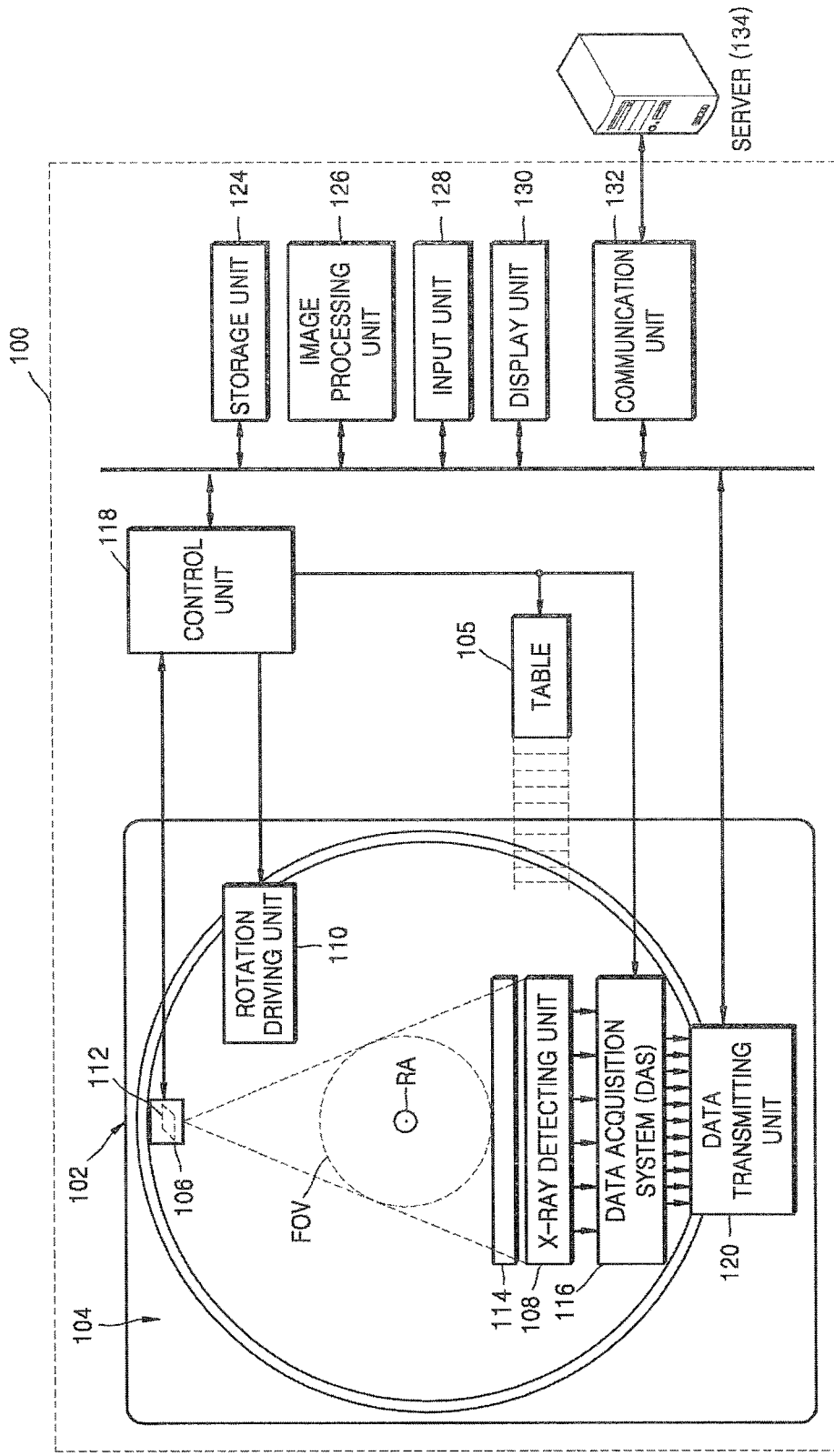
FIG. 2 illustrates a structure of a CT system according to an exemplary embodiment.

FIG. 2 is a block diagram illustrating a structure of the CT system 100.

The CT system 100 may include the gantry 102, the table 105, a control unit 118, a storage unit 124, an image processing unit 126, an input unit 128, a display unit 130, and a communication unit 132.

As described above, the object 10 may be positioned on the table 105. In the present embodiment, the table 105 may move in a predetermined direction (e.g., at least one of up, down, right, and left), and movement of the table 105 may be controlled by the control unit 118.

The gantry 102 may include a rotating frame 104, the X-ray generating unit 106, the X-ray detecting unit 108, a rotation driving unit 110, a data acquisition system (DAS) 116, and a data transmitting unit 120. The rotating frame 104 may have a loop shape capable of rotating with respect to a predetermined rotation axis RA. Also, the rotating frame 104 may have a disc shape.

The rotating frame 104 may include the X-ray generating unit 106 and the X-ray detecting unit 108 that are arranged to face each other so as to have predetermined fields of view (FOV). The rotating frame 104 may also include an anti-scatter grid 114. The anti-scatter grid 114 may be positioned between the X-ray generating unit 106 and the X-ray detecting unit 108.

In a medical imaging system, X-ray radiation that reaches a detector (or a photosensitive film) includes not only attenuated primary radiation that forms a valuable image but also scattered radiation that deteriorates the quality of an image.

In order to transmit most of the primary radiation and to attenuate the scattered radiation, the anti-scatter grid 114 may be positioned between a patient and the detector (or the photosensitive film). For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driving unit 110 and may rotate the X-ray generating unit 106 and the X-ray detecting unit 108 at a predetermined rotation speed. The rotating frame 104 may receive the driving signal and power from the rotation driving unit 110 while the rotating frame 104 contacts the rotation driving unit 110 via a slip ring (not shown). Also, the rotating frame 104 may receive the driving signal and power from the rotation driving unit 110 via wireless communication.

The X-ray generating unit 106 may receive power to generate and emit X-rays. The power may be received from a power distribution unit (PDU) (not shown) via a slip ring (not shown) and then a high voltage generating unit (not shown).

When the high voltage generating unit applies predetermined voltage (hereinafter, referred to as a tube voltage) to the X-ray generating unit 106, the X-ray generating unit 106 may generate X-rays having energy spectra that correspond to the tube voltage. The X-ray generated by the X-ray generating unit 106 may be emitted in a predetermined form due to a collimator 112. The collimator 112 may be part of, for example, the X-ray generating unit 106. The X-ray detecting unit 108 may be positioned to face the X-ray generating unit 106. There may be a plurality of X-ray detecting devices where each may establish one channel, but embodiments of the disclosure are not limited thereto. Each X-ray detecting device may be, for example, the X-ray detecting unit 108, or the X-ray detecting unit 108 may comprise a plurality of X-ray detecting devices.

The X-ray detecting unit 108 may detect the X-ray transmitted by the X-ray generating unit 106 through the object 10, and the X-ray detecting unit 108 may generate an electrical signal corresponding to intensity of the detected X-ray. The X-ray detecting unit 108 may include an indirect-type X-ray detector for detecting radiation after converting the radiation into light, and/or a direct-type X-ray detector for detecting radiation after directly converting the radiation into electric charges. The indirect-type X-ray detector may use a scintillator, while the direct-type X-ray detector may use a photon counting detector.

The DAS 116 may be connected to the X-ray detecting unit 108. Electrical signals generated by the X-ray detecting unit 108 may be acquired by the DAS 116. The electrical signals generated by the X-ray detecting unit 108 may be provided to an analog-to-digital converter (not shown) via an amplifier (not shown).

According to a slice thickness or the number of slices, only some of a plurality of pieces of data collected by the X-ray detecting unit 108 may be provided to the image processing unit 126 via the data transmitting unit 120, or the image processing unit 126 may select only some of the plurality of pieces of data. Such a digital signal may be provided to the image processing unit 126 via the data transmitting unit 120. The digital signal may be provided to the image processing unit 126 by wire or wirelessly.

The control unit 118 may control operation of each of the elements in the CT system 100. For example, the control unit 118 may control operations of the table 105, the rotation driving unit 110, the collimator 112, the DAS 116, the storage unit 124, the image processing unit 126, the input unit 128, the display unit 130, the communication unit 132, or the like.

The image processing unit 126 may receive data acquired by the DAS 116 (e.g., raw data before processing) via the data transmitting unit 120, and may perform pre-processing. The pre-processing may include, for example, correcting a sensitivity irregularity between channels and a process of correcting signal loss due to a rapid decrease in signal strength or due to the presence of an X-ray absorbing material such as metal. Data output from the image processing unit 126 may be referred to as raw data or projection data.

The projection data may be stored in the storage unit 124 with imaging conditions (e.g., the tube voltage, an imaging angle, etc.) during the acquisition of data. The projection data may be a group of data values that correspond to the intensity of the X-ray that has passed through the object 10. For convenience of description, a group of a plurality of pieces of projection data that are simultaneously obtained from all channels at the same imaging angle is referred to as a projection data set.

The storage unit 124 may include at least one storage medium from, for example, flash memory-type storage medium, hard disk-type storage medium, multimedia card micro-type storage medium, card-type memories (e.g., a Secure Digital (SD) card, an eXtreme Digital (XD) card, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processing unit 126 may reconstruct a cross-sectional image of the object 10 by using the acquired projection data set. The cross-sectional image may be a 3D image. In other words, the image processing unit 126 may reconstruct a 3D image of the object 10 by using a cone beam reconstruction method or the like, based on the acquired projection data set.

The input unit 128 may receive an external input with respect to an X-ray tomography imaging condition, an image processing condition, or the like. For example, the X-ray tomography imaging condition may include tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, or the like. The image processing condition may include a resolution of an image, an attenuation coefficient setting for the image, setting for an image combining ratio, or the like.

The input unit 128 may also include a device for receiving a predetermined input from an external source. For example, the input unit 128 may include a microphone, a keyboard, a mouse, a joystick, a touch pad, a touch pen, a voice recognition device, a gesture recognition device, or the like.

The display unit 130 may display an X-ray image reconstructed by the image processing unit 126.

Exchanges of data, power, or the like between the aforementioned elements may be performed by using wired and/or wireless communication, including optical communication. The communication unit 132 may perform communication with an external device, an external medical apparatus, etc. via a server 134 or the like.

The communication will now be described with reference to FIG. 3.

Figure 3:
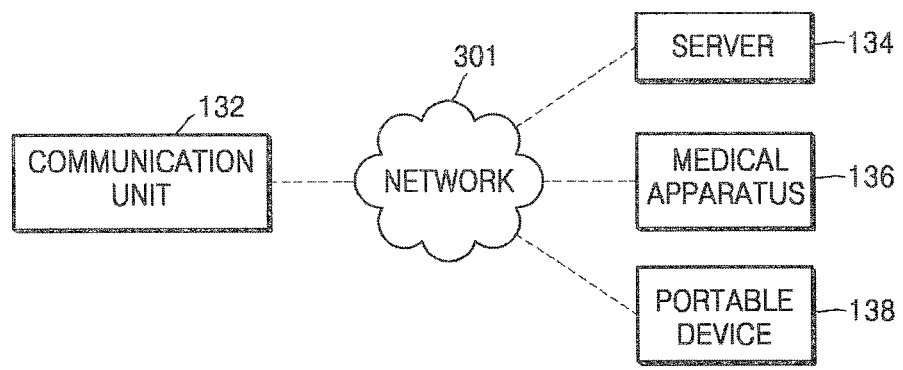
FIG. 3 illustrates a configuration of a communication unit.

FIG. 3 is a block diagram illustrating the communication performed by the communication unit 132.

The communication unit 132 may be connected wirelessly or via wire to a network 301 and therefore may perform communication with the server 134, a medical apparatus 136, and/or a portable device 138.

Accordingly, the communication unit 132 may be able to exchange data with a hospital server or another medical apparatus in a hospital via a picture archiving and communication system (PACS). Also, the communication unit 132 may perform data communication with the portable device 138 or the like according to the digital imaging and communications in medicine (DICOM) standard. The communication unit 132 may transmit and receive data related to diagnosing the object 10 via the network 301.

The communication unit 132 may also transmit and receive a medical image obtained from the medical apparatus 136 such as a magnetic resonance imaging (MRI) apparatus, an X-ray apparatus, or the like. Furthermore, the communication unit 132 may receive a diagnosis history or a medical treatment schedule about a patient from the server 134 to help diagnose the patient.

The communication unit 132 may perform data communication not only with the server 134 or the medical apparatus 136 in a hospital but also with the portable device 138 of a user or patient. Furthermore, the communication unit 132 may transmit information about device error, information about quality control status, or the like to a system manager or a service manager via the network 301, and may receive feedback regarding the information from the system manager or service manager.

Figure 4:
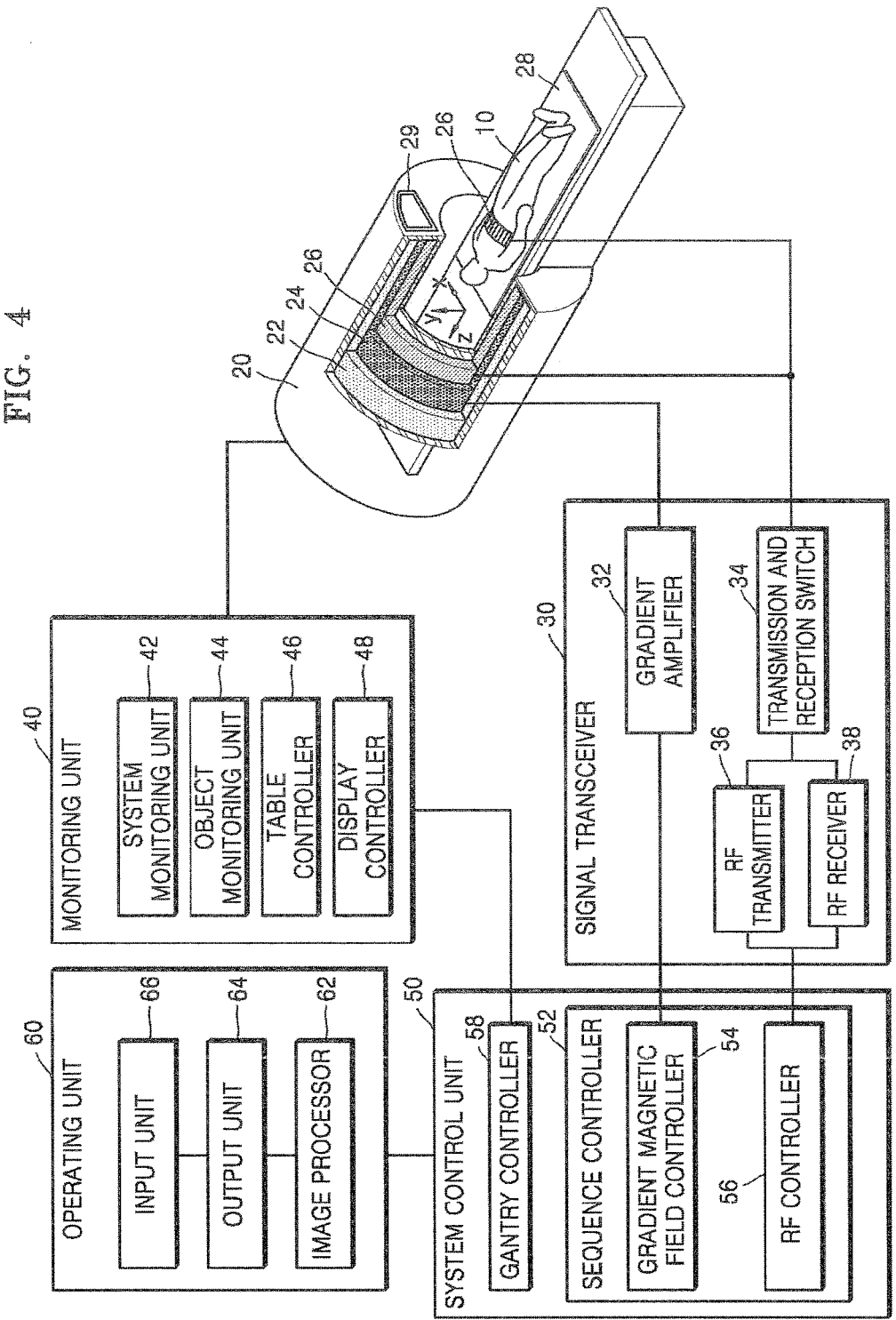
FIG. 4 is a schematic diagram of a general magnetic resonance imaging (MRI) system.

FIG. 4 is a block diagram of a general MRI system. In the present disclosure, an "MR image" refers to an image of an object obtained by using the nuclear magnetic resonance principle. Furthermore, a "pulse sequence" refers to signals repeatedly applied by an MRI apparatus. The pulse sequence may include a time parameter of a radio frequency (RF) pulse, for example, repetition time (TR) or echo time (TE). Additionally, a "pulse sequence schematic diagram" shows an order of events that occur in an MRI apparatus. For example, the pulse sequence schematic diagram may be a diagram showing an RF pulse, a gradient magnetic field, an MR signal, or the like with respect to time.

An MRI system is an apparatus for acquiring a sectional image of a part of an object by expressing, in a contrast comparison, a strength of a MR signal with respect to a radio frequency (RF) signal generated in a magnetic field having a specific strength.

For example, if an RF signal that only resonates a specific atomic nucleus (for example, a hydrogen atomic nucleus) is emitted for an instant toward the object placed in a strong magnetic field and then such emission stops, an MR signal is emitted from the specific atomic nucleus, and thus the MRI system may receive the MR signal and acquire an MR image. The MR signal denotes an electromagnetic signal emitted from the object.

An intensity of the MR signal may be determined according to a density of a predetermined atom (for example, hydrogen) of the object, a relaxation time T1, a relaxation time T2, and a flow of blood or the like. MRI systems include characteristics different from those of other imaging apparatuses.

Unlike imaging apparatuses such as CT apparatuses that acquire images according to a direction of detection hardware, MRI systems may acquire 2D images or 3D images that are oriented toward an optional point.

MRI systems do not expose objects or examiners to radiation, unlike CT apparatuses, X-ray apparatuses, position emission tomography (PET) apparatuses, and single photon emission CT (SPECT) apparatuses. MRI systems may acquire images having high soft tissue contrast, and may acquire neurological images, intravascular images, musculoskeletal images, and oncologic images that are required to precisely capture abnormal tissues.

Referring to FIG. 4, the general MRI system may include a gantry 20, a signal transceiver 30, a monitoring unit 40, a system control unit 50, and an operating unit 60.

The gantry 20 prevents external emission of electromagnetic waves generated by a main magnet 22, a gradient coil 24, and an RF coil 26. A magnetostatic field and a gradient magnetic field are formed in the gantry 20, and an RF signal is emitted toward an object 10. The main magnet 22, the gradient coil 24, and the RF coil 26 may be arranged in a predetermined direction in the gantry 20. The predetermined direction may be, for example, a coaxial direction of the gantry 20.

The object 10 may be disposed on a table 28 that is capable of going in to the gantry 20. The main magnet 22 generates a magnetostatic field or a static magnetic field for aligning magnetic dipole moments of atomic nuclei of the object 10 in a constant direction. A precise and accurate MR image of the object 10 may be obtained due to a strong and uniform magnetic field generated by the main magnet 22.

The gradient coil 24 includes X, Y, and Z coils for generating gradient magnetic fields in X-, Y-, and Z-axis directions at right angles to each other. The gradient coil 24 may provide location information of each region of the object 10 by inducing resonance frequencies differently according to the regions of the object 10.

The RF coil 26 may emit an RF signal toward a patient and receive an MR signal emitted from the patient. In detail, the RF coil 26 may transmit toward the patient an RF signal to excite the atomic nuclei in the targeted area to a higher state. When the RF transmission is stopped, the atomic nuclei may drop to the lower state and emit energy as MR signals. The RF coil may receive the MR signals from the targeted area of the patient.

For example, in order to transit an atomic nucleus from a low energy state to a high energy state, the RF coil 26 may generate and apply an RF signal corresponding to the atomic nucleus of the target area of the object 10. When the electromagnetic wave signal generated by the RF coil 26 is applied to the atomic nucleus, the atomic nucleus may transition from a low energy state to a high energy state.

Then, when the RF coil 26 stops generating electromagnetic waves, the atomic nucleus may transition from the high energy state to the low energy state, and emits electromagnetic waves having a Lamor frequency.

The RF coil 26 may receive electromagnetic waves from atomic nuclei in the object 10. The RF coil 26 may be realized as a RF transceiver that is able to transmit and receive RF signals. The RF coil 26 may generate electromagnetic waves having a frequency that corresponds to a type of an atomic nucleus and receive electromagnetic waves emitted by the atomic nuclei.

Alternatively, the RF coil 26 may be realized as a transmission RF coil able to generate electromagnetic waves having a frequency that corresponds to a type of atomic nuclei, and a reception RF coil able to receive electromagnetic waves emitted by atomic nuclei.

The RF coil 26 may be fixed to the gantry 20 or may be detachable. When the RF coil 26 is detachable, the RF coil 26 may be an RF coil for a specific part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly, and may also perform dual tune communication according to a communication frequency band. The RF coil 26 may be a birdcage coil, a surface coil, or a transverse electromagnetic (TEM) coil according to design and implementation criteria.

The RF coil 26 may be a transmission exclusive coil, a reception exclusive coil, or a transmission and reception coil. The RF coil 26 may be an RF coil having various numbers of channels, such as 16 channels, 32 channels, 72 channels, and 144 channels.

The gantry 20 may further include a display 29 disposed outside the gantry 20 and a display (not shown) disposed inside the gantry 20. The gantry 20 may provide predetermined information to the user or the object 10 through the display 29 and the display inside the gantry 20, respectively.

The signal transceiver 30 may control the gradient magnetic field formed inside the gantry 20, i.e., in the bore, according to a predetermined MR sequence, and control transmission and reception of RF signal and MR signal. The signal transceiver 30 may include a gradient amplifier 32, a transmission and reception switch 34, an RF transmitter 36, and an RF receiver 38.

The gradient amplifier 32 drives the gradient coil 24 included in the gantry 20, and may supply a pulse signal for generating a gradient magnetic field to the gradient coil 24 under the control of a gradient magnetic field controller 54. By controlling the pulse signal supplied from the gradient amplifier 32 to the gradient coil 24, gradient magnetic fields in X-, Y-, and Z-axis directions may be synthesized.

The RF transmitter 36 and the RF receiver 38 may drive the RF coil 26. The RF transmitter 36 may supply an RF pulse in a Lamor frequency to the RF coil 26, and the RF receiver 38 may receive an MR signal received by the RF coil 26.

The transmission and reception switch 34 may control transmitting the RF signal and receiving the MR signal. For example, the transmission and reception switch 34 may allow transmission of the RF signal toward the object 10 through the RF coil 26 during a transmission mode, and allow reception of the MR signal from the object 10 through the RF coil 26 during a reception mode. The transmission and reception switch 34 may be controlled by a control signal from an RF controller 56.

The monitoring unit 40 may monitor or control the gantry 20 or devices mounted on the gantry 20. The monitoring unit 40 may include a system monitoring unit 42, an object monitoring unit 44, a table controller 46, and a display controller 48.

The system monitoring unit 42 may monitor and control a state of the magnetostatic field, a state of the gradient magnetic field, a state of the RF signal, a state of the RF coil 26, a state of the table 28, a state of a device measuring body information of the object 10, a power supply state, a state of a thermal exchanger, and a state of a compressor.

The object monitoring unit 44 may monitor a state of the object 10. In detail, the object monitoring unit 44 may include a camera for observing movement or position of the object 10, a respiration measurer for measuring the respiration of the object 10, an electrocardiogram (ECG) measurer for measuring the electrical activity of the object 10, or a thermometer for measuring a temperature of the object 10.

The table controller 46 controls a movement of the table 28 where the object 10 is positioned. The table controller 46 may control the movement of the table 28 according to a sequence control of a sequence controller 52. For example, during moving imaging of the object 10, the table controller 46 may continuously or discretely move the table 28 according to the sequence control of the sequence controller 52, and thus the object 10 may be photographed in a field of view (FOV) larger than that of the gantry 20.

The display controller 48 controls the display 29 outside the gantry 20 and the display inside the gantry 20. In detail, the display controller 48 may turn the display 29 and the inside display on or off, and may control a screen image to be output on the display 29 and the inside display. Also, when a speaker is located inside or outside the gantry 20, the display controller 48 may turn the speaker on or off, and/or may control sound to be output via the speaker.

The system control unit 50 may include the sequence controller 52 for controlling a sequence of signals formed in the gantry 20, and a gantry controller 58 for controlling the gantry 20 and the devices mounted on the gantry 20. The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating unit 60.

The pulse sequence may include all information required to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating unit 60 may request the system control unit 50 to transmit pulse sequence information while controlling an overall operation of the MRI system. The operating unit 60 may include an image processor 62 for receiving and processing the MR signal received by the RF receiver 38, an output unit 64, and an input unit 66.

The image processor 62 may process the MR signal received from the RF receiver 38 so as to generate MR image data of the object 10. The image processor 62 receives the MR signal received by the RF receiver 38 and performs any one of various signal processing, such as amplification, frequency transformation, phase detection, low frequency amplification, and filtering, on the received MR signal.

The image processor 62 may arrange digital data in a k space (also referred to as a Fourier space or a frequency space) of a memory, and rearrange the digital data into image data via 2D or 3D Fourier transformation. The image processor 62 may perform a composition process or a difference calculation process on the image data if required.

The composition process may be an addition process performed on a pixel or a maximum intensity projection (MIP) process performed on a pixel. The image processor 62 may store not only the rearranged image data but also image data on which a composition process or a difference calculation process is performed, in memory (not shown) or an external server.

The image processor 62 may perform any of the signal processes on the MR signal in parallel. For example, the image processor 62 may perform a signal process on a plurality of MR signals received by a multi-channel RF coil in parallel so as to rearrange the plurality of MR signals into image data.

The output unit 64 may output image data generated or rearranged by the image processor 62 to the user. The output unit 64 may also output information required for the user to manipulate the MRI system, such as a user interface (UI), user information, or object information. The output unit 64 may be a speaker, a printer, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a flat panel display (FPD), a 3-dimensional (3D) display, a transparent display, or any one of other various output devices that are well known to one of ordinary skill in the art.

The user may input object information, parameter information, a scan condition, a pulse sequence, or information about image composition or difference calculation by using the input unit 66. The input unit 66 may be a keyboard, a mouse, a track ball, a voice recognizer, a gesture recognizer, a touch screen, or any one of other various input devices that are well known to one of ordinary skill in the art.

The signal transceiver 30, the monitoring unit 40, the system control unit 50, and the operating unit 60 are separate components in FIG. 4, but it will be obvious to one of ordinary skill in the art that respective functions of the signal transceiver 30, the monitoring unit 40, the system control unit 50, and the operating unit 60 may be performed by another component.

For example, the image processor 62 may convert the MR signal received from the RF receiver 38 into a digital signal, but alternatively, the conversion of the MR signal into the digital signal may be performed by the RF receiver 38 or the RF coil 26.

The gantry 20, the RF coil 26, the signal transceiver 30, the monitoring unit 40, the system control unit 50, and the operating unit 60 may be connected to each other by wire or wirelessly. When they are connected wirelessly, the MRI system may further include an apparatus (not shown) for synchronizing clock signals therebetween.

Communication between the gantry 20, the RF coil 26, the signal transceiver 30, the monitoring unit 40, the system control unit 50, and the operating unit 60 may be performed by using a high-speed digital interface such as low voltage differential signaling (LVDS), asynchronous serial communication using, for example, a universal asynchronous receiver transmitter (UART), a low-delay network protocol such as error synchronous serial communication or a controller area network (CAN), optical communication, or any of other various communication methods that are well known to one of ordinary skill in the art.

Furthermore, the MRI system of FIG. 4 may include a communication unit (not shown). The communication unit may be connected to at least one of the gantry 20, the signal transceiver 30, the monitoring unit 40, the system control unit 50, and the operating unit 60 of FIG. 4.

The communication unit may transmit and receive data to and from a hospital server or another medical apparatus in a hospital, which is connected through a picture archiving and communication system (PACS), and perform data communication according to the digital imaging and communications in medicine (DICOM) standard. Since the communication unit corresponds to the communication unit 132 described with reference to FIG. 3, a detailed description thereof will not be repeated below.

A medical image processing apparatus according to an exemplary embodiment may be any medical image processing apparatus capable of processing an MR image, a CT image, an X-ray image, or an ultrasound image respectively obtained by an MRI apparatus, a CT apparatus, an X-ray apparatus, or an ultrasound diagnosis apparatus to generate a diagnostic image so that a user may diagnose a patient's disease.

In detail, a medical image processing apparatus according to an exemplary embodiment processes a medical image obtained via a medical image capturing apparatus for obtaining a medical image, such as the CT system 100 or the MRI system described with reference to FIGS. 1 through 4, and generates a diagnostic image so that the user may diagnose a patient's disease. In detail, the medical image processing apparatus may be included in the CT system 100 or MRI system described with reference to FIGS. 1 through 4 to process a CT or MR image.

Furthermore, a medical image processing apparatus according to an exemplary embodiment may receive a CT or MR image from the CT system 100 or MRI system that is externally connected thereto and obtain a diagnostic image by processing the received CT or MR image.

Figure 5A:
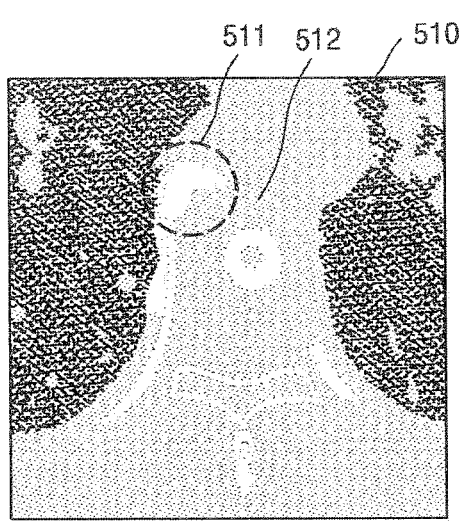
FIGS. 5A and 5B show CT images for diagnosing metastatic bone cancer.
Figure 5B:
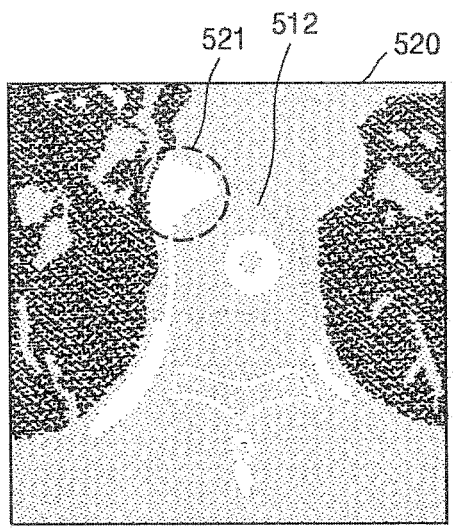

FIGS. 5A and 5B show CT images for diagnosing a metastatic bone cancer.

As cancers progress in various organs such as breast, prostate, etc., they may spread to bones. In detail, 30% to 85% of cancers metastasize to bones and cause complications that may lead to pain, paralysis, impairment, etc. For early diagnosis of metastatic bone cancer, it is necessary to perform a follow-up examination at six-month intervals or less to check whether the metastatic bone cancer has progressed.

To perform the follow-up examination, the user has to compare a plurality of medical images acquired at different dates. When the medical images are captured for the same patient at different dates, the medical images may differ from one another partly due to posture, position, etc. of the patient being imaged. Accordingly, a doctor may have difficulty in identifying the progression of the metastatic bone cancer when visually comparing a first CT image and a second CT image taken 6 months apart.

FIGS. 5A and 5B show CT images representing cross-sections of a chest of the same patient. In detail, FIG. 5A shows a first CT image 510 acquired by performing a CT scan, and FIG. 5B shows a second CT image 520 acquired by performing a CT scan at a later date. While "date" implies a different day, the disclosure does not restrict any embodiment to such an implication. The word "date" has been chosen for the sake of clarity, but subsequent images may be from the same day. The term "time point" may be used as an alternative to the term "date."

Referring to FIGS. 5A and 5B, a metastatic bone cancer 511 can be seen near the vertebra 512 in the first CT image 510, and a metastatic bone cancer 521 can be seen near the vertebra 512 in the second CT image 520. To monitor and diagnose whether the metastatic bone cancers 511 and 521 have progressed between the first and second dates, the user, e.g., a medical practitioner, has to visually compare the first CT image 510 with the second CT image 520.

By comparing the first CT image 510 to the second CT image 520, it can be seen that a size of the metastatic bone cancer 511 in the first CT image 510 is larger than that of the metastatic bone cancer 521 in the second CT image 520. However, the user may have difficulty in accurately determining the degree of progression of the metastatic bone cancers 511 and 521 by comparing the first CT image 510 to the second CT image 520.

As described above, follow-up monitoring of the metastatic bone cancers 511 and 521 may be required to diagnose the progression of the metastatic bone cancers 511 and 521. In detail, it may be necessary to scan an object at a plurality of dates to observe how an object or a target in the object has changed over time. For example, if an abnormal tissue requires follow-up monitoring, the user may have to observe a change in the abnormal tissue at predetermined time intervals, thereby determining whether treatment of the tissue is needed or how the abnormal tissue is changing.

In detail, since metastatic bone cancer is accompanied by a change in bone, the progression of the metastatic bone cancer may be monitored by observing the change. Thus, it may be determined by observing a change in bone status whether the metastatic bone cancer has worsened or whether a size of an area affected by the metastatic bone cancer has changed. For ease of explanation, it is hereinafter assumed that a target requiring follow-up monitoring is a bone in an object.

A medical image processing apparatus configured to generate a diagnostic image so that a user may easily identify or recognize the degree of change in a target will now be described in detail with reference to FIGS. 6 through 18.

Figure 6:
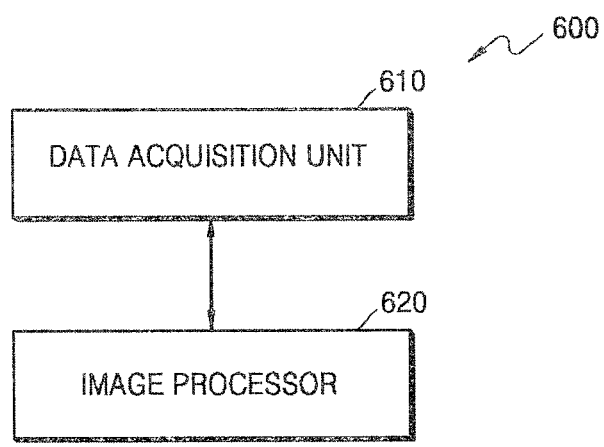
FIG. 6 illustrates a medical image processing apparatus according to an exemplary embodiment.

FIG. 6 illustrates a medical image processing apparatus 600 according to an exemplary embodiment. The medical image processing apparatus 600 includes a data acquisition unit 610 and an image processor 620. The medical image processing apparatus 600 may be any medical image processing apparatus that is capable of receiving and processing a medical image.

For example, the medical image processing apparatus 600 may be included in the CT system 100 described with reference to FIGS. 1 and 2. Accordingly, the medical image processing apparatus 600 may be similar to the image processing unit 126 described with reference to FIG. 2. The image processing unit 126, therefore, may also include the data acquisition unit 610 and the image processor 620.

Furthermore, the medical image processing apparatus 600 may be included in the medical apparatus 136 or the portable device 138 and connect to the CT system 100. The medical image processing apparatus 600 may be any medical imaging apparatus that is capable of acquiring and processing a CT image. The medical image processing apparatus 600 may process a CT image, an optical coherence tomography (OCT) image, or a positron emission tomography (PET) image acquired via a CT apparatus, an OCT apparatus, or a PET-CT apparatus, respectively, to generate a diagnostic image. An example where a diagnostic image is generated using a CT image will be described in detail below.

The medical image processing apparatus 600 may also be included in the MRI system described with reference to FIG. 4. If the medical image processing apparatus 600 is included in the MRI system, the data acquisition unit 610 and the image processor 620 may correspond to the image processor 62 described with reference to FIG. 4.

The data acquisition unit 610 may acquire a plurality of medical images representing an object including at least one target at different dates. The object may be a patient's body part or at least one organ. The target may be included in the object and may be at least one of specific tissue, organ, body part, and region of interest (ROI) that requires follow-up monitoring. For example, the object may be a patient's abdomen or chest, and the target may be a bone in the abdomen region or the chest region, respectively. As another example, the target may be a metastatic bone cancer or malignant tumor.

If there is metastatic bone cancer at a bone in a patient's chest, the user needs to monitor the metastatic bone cancer over time. Accordingly, the image processor 620 may acquire diagnostic images showing the degree of change in the target bone at various dates.

For example, the data acquisition unit 610 may perform medical imaging of an object and then again at a later date. The successive imaging may occur at a specific time interval for follow-up monitoring. The data acquisition unit 610 may receive image data to directly generate the first and second medical images, or the data acquisition unit 610 may receive first and second medical images from another source. Furthermore, the first and second images may be medical images or multi-dimensional data consisting of image elements (pixel or voxel values) that can be used to generate the medical images.

The image processor 620 may generate a diagnostic image based on the plurality of medical images acquired by the data acquisition unit 610, showing the degree of change that has occurred in the target over time. The degree of change in the target may be for one or more properties of the target. For example, the change may include physiological change, position change, size change, and/or shape change.

In detail, when the target is a bone in the patient's body, the diagnostic image may be an image showing the degree of change in the bone, which may be classified into one of a plurality of stages. Furthermore, the diagnostic image may be an image representing the degree of progression of a metastatic bone cancer including at least one of a lytic metastatic cancer and a blastic metastatic cancer.

Figure 7:
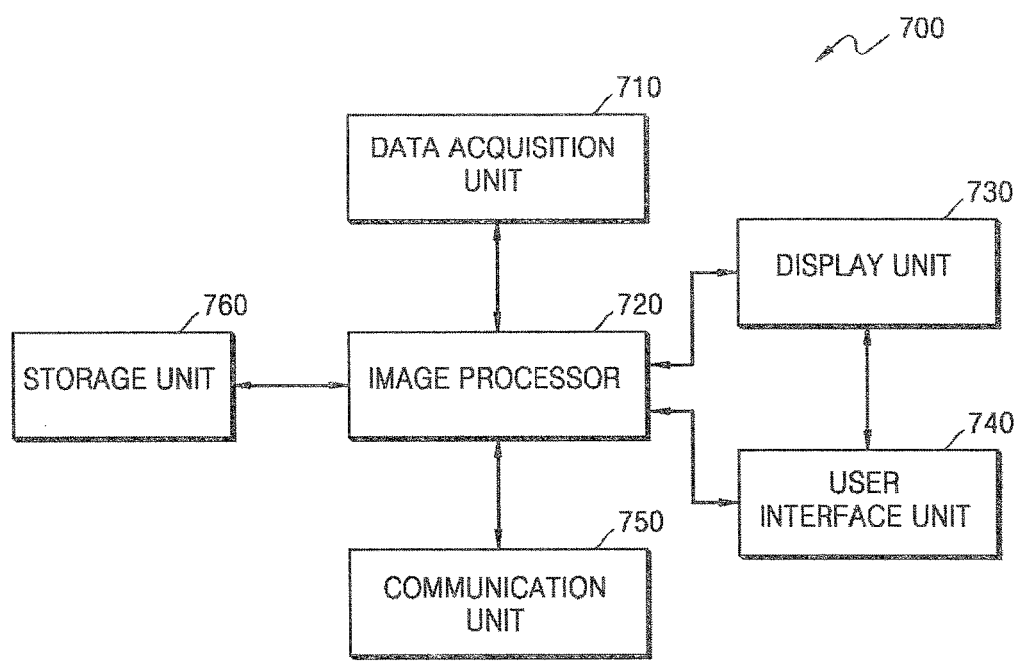
FIG. 7 illustrates a medical image processing apparatus according to another exemplary embodiment.

FIG. 7 illustrates a medical image processing apparatus 700 according to another exemplary embodiment.

Referring to FIG. 7, the medical image processing apparatus 700 includes a data acquisition unit 710 and an image processor 720. Since the data acquisition unit 710 and the image processor 720 may correspond to the data acquisition unit 610 and the image processor 620, respectively, descriptions already provided with reference to FIG. 6 will be omitted below. The medical image processing apparatus 700 may further include at least one of a display unit 730, a user interface unit 740, a communication unit 750, and a storage unit 760. Since the display unit 730, the user interface unit 740, the communication unit 750, and the storage unit 760 have the same configurations and functions as the display unit 130, the input unit 128, the communication unit 132, and the storage unit 124, respectively, of the CT system 100, descriptions already provided with reference to FIG. 2 will be omitted below.

The data acquisition unit 710 acquires a plurality of medical images of an object including at least one target at a plurality of different dates. It is hereinafter assumed that the data acquisition unit 710 acquires two medical images representing an object at two different dates.

The data acquisition unit 710 may obtain a first medical image by performing medical imaging of an object and a second medical image by performing medical imaging of the object at a later date. In this case, the first and second medical images may be the same type of medical images acquired by imaging the same object. For example, the first and second medical images may be CT images obtained by performing a CT scan on the same patient. Alternatively, the first and second medical images may be MR images obtained by performing MRI on the same patient. It is hereinafter assumed that the first and second medical images are CT images.

The image processor 720 may generate a diagnostic image showing the degree of change in the target over time, based on the plurality of medical images acquired by the data acquisition unit 710. For example, the change to the target may include physiological change, position change, size change, and shape change. For convenience of explanation, the degree to which the target(s) has changed over time is hereinafter referred to as the "degree of change."

The image processor 720 may classify the degree of change in the target(s) into a plurality of stages and generate a diagnostic image that can distinguish one stage from another. In this case, the plurality of stages may be classified as no change, formation, or destruction.

Metastatic bone cancers are classified into lytic metastatic cancer destroying bones and blastic metastatic cancer forming bones. As bone metastasis progresses, lytic metastatic cancer destroys bone. During progression of bone metastasis, blastic metastatic cancer forms bone. Thus, the image processor 720 can generate a diagnostic image that can show the effects of each stage to allow classifying the degree of change caused by metastatic bone cancer into one of the three stages.

Furthermore, the image processor 720 may generate a plurality of registered medical images by registering a plurality of medical images. Image registration is a process of adjusting a plurality of images to have the same sizes and views so they can be compared easily. The image processor 720 may also quantify the degree of change based on a variation in pixel intensity between the registered medical images and generate a diagnostic image showing the quantified stages in such a manner that they are distinguished from one another. Accordingly, variation in pixel intensity between one registered medical image and a later acquired registered medical image can lead to classification as, for example, no change stage, bone formation stage, or bone destruction stage.

Signal intensity on a CT image varies depending on properties of tissue in a medical image. In detail, a CT image is expressed in Hounsfield Units (HU) as a measure radiodensity of materials, where the radiodensity measurement can range from −1000 HU to +3000 HU. For example, air is defined as −1000 HU and water as 0 HU. The HU values may increase from air to fat to soft muscle tissue to bone. That is, the more dense material has a higher HU value and appears to be brighter on a CT image. Accordingly, a bone in a CT image appears brighter than softer tissues.

Thus, the image processor 720 may identify whether a bone has not changed substantially, has grown, or has been destroyed, based on signal intensity difference between registered CT images. An operation of generating registered medical images will be described in detail below with reference to FIGS. 8 through 11.

The display unit 730 may display one or more medical images such as those generated by the image processor 720. The display unit 730 may also act as a user interface. The user may perform setting operations and data entry via a user interface screen displayed by the display unit 730.

The display unit 730 may be any type of device that allows the user to see data. For example, the display unit 730 may be one of a cathode ray tube (CRT) display, a liquid crystal display (LCD), a plasma display panel (PDP) display, an organic light-emitting diode (OLED) display, a field emission display (FED), an LED display, a vacuum fluorescent display (VFD), a digital light processing (DLP) display, a flat panel display (FPD), a 3D display, a transparent display, etc.

The user interface unit 740 may control the user interface screen displayed on the display unit 730 and receive a command or data from a user via the user interface screen. The user interface unit 740 may also include a mouse, a keyboard, or another input device including hard keys for inputting data. The user may enter data or command via, for example, the mouse or the keyboard.

The user interface unit 740 may also support a touch pad. In detail, the user interface unit 740 supports a touch pad (not shown) combined with a display panel (not shown) in the display unit 730 and outputs a user interface screen to the display panel. A command may then be input by the user via the user interface screen.

In detail, if the user interface unit 740 supports a touch pad, when the user touches a point on the user interface screen, the user interface unit 740 detects the touch. The user interface unit 740 may then transmit information about the touched point to the image processor 720. The image processor 720 may recognize a user request or command corresponding to a menu item displayed at the detected point and generates a tomography image according to the user request or command.

The user interface unit 740 may receive information about color mapping that is used to represent the degree of change in a target in a diagnostic image.

The communication unit 750 may perform communication with an external device, an external medical apparatus, etc. For example, the communication unit 750 may be connected to at least one of external X-ray apparatus, medical apparatus, server, and portable medical device. In detail, the communication unit 750 may be connected to an external medical imaging apparatus to receive a medical image. Furthermore, since the communication unit 750 may correspond to the communication unit 132 described with reference to FIG. 3, descriptions already provided with reference to FIG. 3 will be omitted below.

In detail, the communication unit 750 may be connected to the network (301 of FIG. 3) by wire or wirelessly to communicate with external devices such as the server (134 of FIG. 3), the medical apparatus (136 of FIG. 3), or the portable device (138 of FIG. 3). The communication unit 750 may exchange data with a hospital server or other medical apparatuses in a hospital connected via a picture archiving and communication system (PACS).

Furthermore, the communication unit 750 may perform data communication with an external device using the digital imaging and communications in medicine (DICOM) standard.

The communication unit 750 may transmit and receive data related to a diagnosis to an object via the network 301. The communication unit 750 may also receive a plurality of medical images obtained from another medical apparatus (136 of FIG. 3) such as an MRI apparatus, a CT apparatus, an X-ray apparatus, or the like. The image processor 720 may receive the plurality of medical images received via the communication unit 750 and generate a diagnostic image.

Furthermore, the communication unit 750 may receive a diagnosis history or a medical treatment schedule about a patient from the server 134 and may use the diagnosis history or the medical treatment schedule for clinical diagnosis of the patient. Also, the communication unit 750 may perform data communication not only with the server 134 or the medical apparatus 136 in a hospital but also with the portable device 138 of a user or patient.

The communication unit 750 may receive the medical images from the server 134 or medical apparatus 136 connected via the network 301 and transmit the received medical images to the data acquisition unit 710. Furthermore, the communication unit 750 may transmit the diagnostic image generated by the image processor 720 to at least one of the server 134, the medical apparatus 136, and the portable device 138, so that the diagnostic image may be displayed at another facility.

The storage unit 760 may store a plurality of medical images. The storage unit 760 may also store various data, programs, etc., necessary for generating a diagnostic image, as well as a final generated diagnostic image. In detail, the storage unit 760 may store the medical images, and when generation of a diagnostic image is requested via the user interface unit 740, automatically output the appropriate medical images to the data acquisition unit 710 or image processor 720.

The storage unit 760 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

An operation of the medical image processing apparatus 600 or 700 according to the one or the other exemplary embodiment will now be described in detail with reference to FIGS. 8 through 18.

Figure 8:
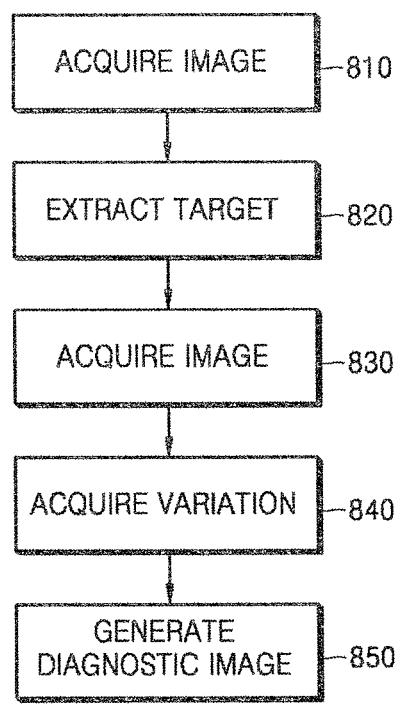
FIG. 8 is a flowchart for explaining an operation of a medical image processing apparatus, according to an exemplary embodiment.
Figure 9:
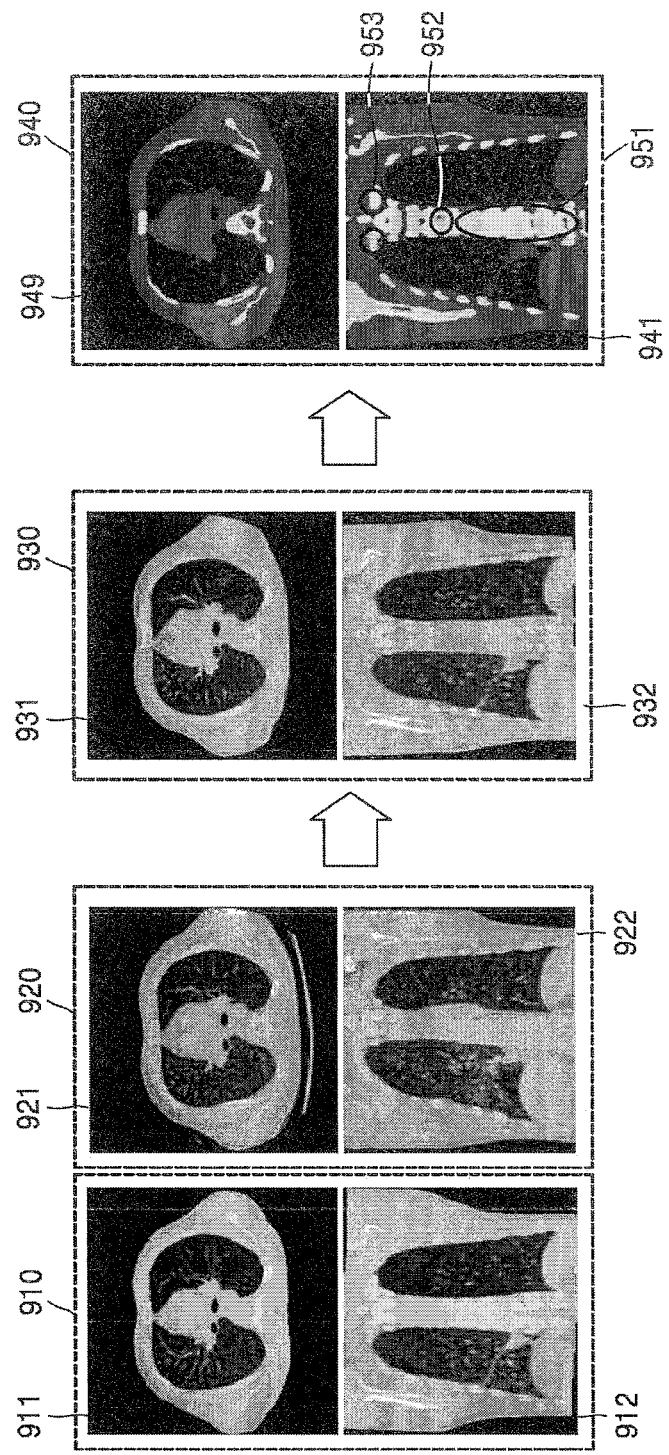
FIG. 9 is a diagram for explaining medical images that are processed by a medical image processing apparatus according to an exemplary embodiment.

FIG. 8 is a flowchart for explaining an operation of the medical image processing apparatus 700, according to an exemplary embodiment, and FIG. 9 is a diagram for explaining medical images that are processed by the medical image processing apparatus 700 according to an exemplary embodiment An operation of the medical image processing apparatus 700 will now be described in detail. Operation of the medical image processing apparatus 600 may be similar to the operation of the medical image processing apparatus 700.

Referring to FIG. 8, the image processor 720 acquires a plurality of medical images (operation 810), each of which may be a 2D or 3D medical image. The image processor 720 extracts at least one target from each of the medical images to obtain a plurality of target-extracted images corresponding to a plurality of time points (operation 820), registers the target-extracted images to thereby generate a plurality of target-registered images (operation 830), and generates a diagnostic image based on the plurality of target-registered images (operations 840 and 850). A "target-extracted image" may be an image obtained by extracting at least one target in the object from each of the plurality of medical images. An image obtained by registering medical images is referred to as a "registered image," and an image obtained by registering target-extracted images is referred to as a "target-registered image." Registering a plurality of images may be normalizing the images for size, shape, position, etc. so that they may be compared to each other.

FIG. 9 shows first medical image 910 and second medical image 920 respectively acquired at first and second time points. The first medical image 910 may include a CT image 911 representing a horizontal cross-section of a chest and a CT image 912 representing the entire chest. Furthermore, the second medical image 920 may similarly include a CT image 921 representing a horizontal cross-section of the chest and a CT image 922 representing the entire chest.

In detail, the image processor 720 extracts a target from each of the plurality of medical images obtained in operation 810. For example, if the target is a bone, a target-extracted image generated by extracting the target is an image of a bone.

The image processor 720 registers the target-extracted images corresponding to a plurality of time points and obtains target-registered images (operation 830). Image registration is the process of matching a plurality of images to one another. In detail, image registration allows a plurality of images to be normalized so that they are similar in size and position. This may allow easy comparison between two or more registered images. For example, image registration may be the process of normalizing the first medical image 910 and the second medical image 920 so that sizes of objects and positions of the objects are similar. Normalizing the different images may allow, for example, superimposing the normalized images. The first medical image 910 and the second medical image 920 may be normalized to acquire a plurality of registered images 930. FIG. 9 shows an example where the second medical image 920 is normalized to the first medical image 910 so that an object in the second medical image 920 has the same position, size, and view as an object in the first medical image 910.

In detail, the image processor 720 may register the plurality of target-extracted images by using at least one of rigid registration and non-rigid registration to generate the plurality of registered images. Rigid registration and non-rigid registration are explained later with respect to FIG. 12. The image processor 720 may measure variations between a plurality of images by using various motion measurement techniques such as optical flow, feature matching, etc., and generates a plurality of registered images by using the measured variations. The registration performed by the image processor 720 will be described in more detail below with reference to FIG. 11.

The image processor 720 may, for example, continuously calculate at least one variation generated in at least one part included in a plurality of targets based on the plurality of registered images (operation 840). For convenience of explanation, a case where the plurality of parts in the plurality of targets is varied is described below. The image processor 720 may also quantify the calculated variations, and classify the degree of change into a plurality of stages based on the quantified variations.

Referring to FIG. 9, the image processor 720 compares the first and second registered images (from the plurality of registered images 930) respectively obtained by registering a first medical image (e.g., the 2D CT image 911) and a second medical image (e.g., the 2D CT image 921), and obtains variations between the first and second registered images. An image 931 obtained by overlaying the first and second registered images is shown in FIG. 9. The image processor 720 may obtain variations between objects in the first and second registered images. For example, the variation may be a value obtained by subtracting a pixel value in the first registered image from a pixel value in the second registered image.

Furthermore, the image processor 720 may obtain variations between targets in a plurality of medical images. To obtain the variations between the targets, the image processor 720 may compare a first target-registered image (not shown), which corresponds to the first time point and is obtained by registering a target-extracted image (not shown) corresponding to the first time point, with a second target-registered image (not shown), which corresponds to the second time point and is obtained by registering a target-extracted image (not shown) corresponding to the second time point.

The image processor 720 may, for example, continuously generate a diagnostic image based on the variations obtained in operation 840 (operation 850). In detail, the image processor 720 may classify the degree of change into a plurality of stages based on the obtained variations and generate a diagnostic image showing the plurality of stages in such a manner as to distinguish them from one another.

In general, when pixels of the later image are compared with pixels of the earlier image, a variation of approximately 0 represents no change in the target, a variation having a negative (−) value represents destruction of the target, and a variation having a positive (+) value represents formation of the target. Thus, the image processor 720 may quantify the variation as three stages, i.e., '0' (no change), '−' (destruction), and '+' (formation) and generate a diagnostic image 940 by indicating the three stages in such a manner that they are distinguished from one another. The image processor 720 may distinguish the stages by, for example, using colors, different shapes, different marks, and/or different lines.

The image processor 720 may generate a diagnostic image showing the degree of change in the target by using colors to differentiate the stages. For example, referring to FIG. 9, the degree of change in a bone that is a target is classified into three stages, and the diagnostic image 940 distinctly shows a stage when no change occurs in the target, a stage when a change occurs in the direction in which the target is formed, and a stage when a change occurs in the direction in which the target is destroyed by using green, red, and blue colors, respectively.

Accordingly, the user may be able to determine at a glance whether the target has changed by destruction or formation. Thus, the user may determine via the diagnostic image 940 the degree of progression of lytic metastatic cancer capable of destroying bone and blastic metastatic cancer capable of forming bone. In this case, the diagnostic image 940 may include overlay images (e.g., the images 931 and 932) obtained by registering and superimposing a plurality of medical images and may be an image indicating on the overlay images (e.g., the images 931 and 932) the degree of change in the target that is classified into a plurality of stages.

Referring to FIG. 9, in a diagnostic image 941 representing the entire chest that is the object, a portion 951 where the target has not changed, a portion 952 where the target has been formed, and a portion 953 where the target has been destroyed may be respectively indicated by green, red, and blue colors.

A diagnostic image may include a target-extracted image representing at least one target in an object and may be an image indicating on the target-extracted image the degree of change that is classified into a plurality of stages. In other words, the diagnostic image may be an image that indicates, on a target-extracted image depicting only a bone in the object, stages of no change in the bone, bone formation, and bone destruction in such a manner as to distinguish the stages from one another.

A diagnostic image may be an enhanced image obtained by enhancing at least one target in one of a plurality of medical images and may be an image indicating on the enhanced image the degree of change that is classified into a plurality of stages. In detail, the image processor 720 may generate the diagnostic image by indicating on an enhanced image obtained by enhancing a target in one of the plurality of medical images so that the target appears clearer, the degree of change in a target that is classified into a plurality of stages as indicated in the diagnostic image 940.

A diagnostic image may be an image indicating on one of a plurality of medical images the degree of change in a target that is classified into a plurality of stages. For example, the diagnostic image may be a blended image obtained by blending at least one of the plurality of medical images with an image showing the degree of change in at least one target. In other words, the diagnostic image may be an image indicating on the blended image the degree of change in a target, where the change is classified into a plurality of stages.

Figure 10:
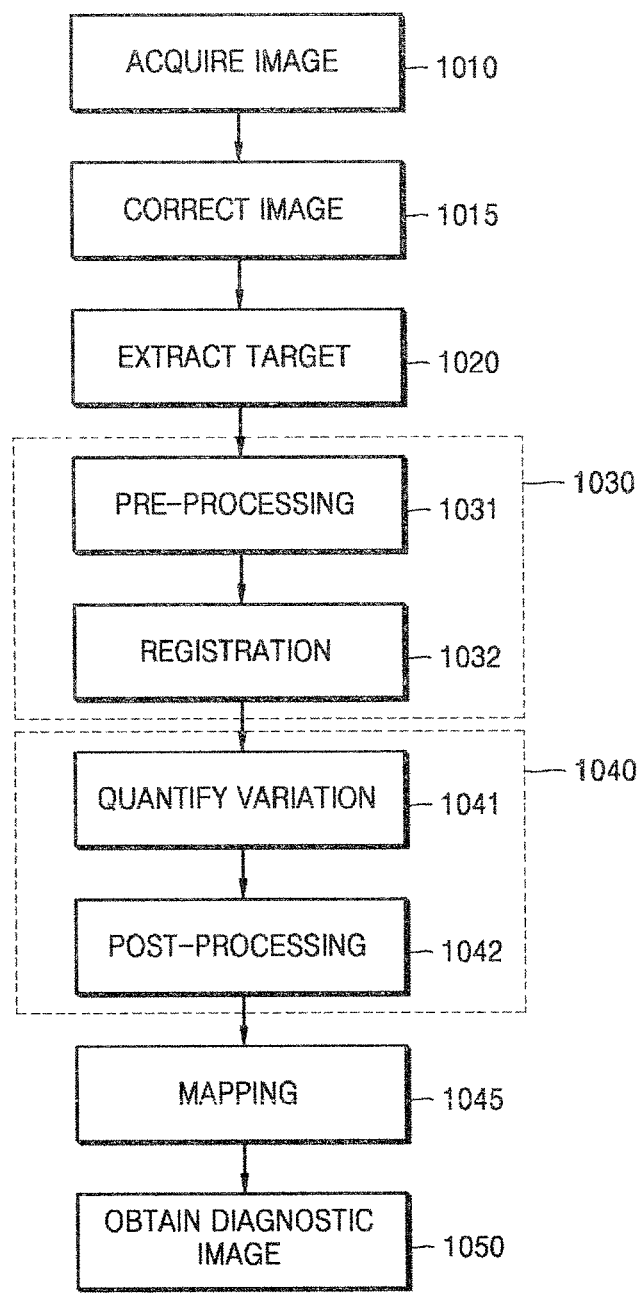
FIG. 10 is a detailed flowchart for explaining an operation of a medical image processing apparatus, according to an exemplary embodiment.

FIG. 10 is a flowchart for explaining an operation of the medical image processing apparatus 700, according to an exemplary embodiment. Since operations 1010, 1020, 1030, 1040, and 1050 in FIG. 10 respectively correspond to operations 810, 820, 830, 840, and 850 described with reference to FIG. 8, descriptions already provided with reference to FIG. 8 will be omitted below.

Referring to FIG. 10, the image processor 720 obtains a plurality of medical images (operation 1010). For example, the image processor 720 may obtain first and second medical images of an object respectively corresponding to first and second time points. Furthermore, when a medical image is obtained for a current time point, the image processor 720 may automatically load at least one medical image obtained at a previous time point to generate a diagnostic image. For example, if generation of a diagnostic image is requested via the user interface unit 740, the image processor 720 may automatically load a plurality of medical images obtained at a predetermined time interval (e.g., six months) from an externally connected server or apparatus. The image processor 720 may keep track of information about where the medical images are stored, and, when generation of a diagnostic image is requested, automatically load the appropriate medical images. The information to locate the stored medical images may be, for example, a web address. When medical images are stored in a PACS, the image processor 720 may automatically copy the medical images from the PACS to the storage unit 760.

The image processor 720 may correct image inhomogeneity among the plurality of medical images (operation 1015). Registration of the plurality of medical images without correcting inhomogeneity may cause errors in registration and quantification. For example, magnetic field inhomogeneity may occur in MR images due to a difference in time when the MR images are captured. The magnetic field inhomogeneity may in turn cause intensity inhomogeneity between a plurality of MR images captured at different times, in which signal intensities vary across the MR images. The image processor 720 may correct intensity inhomogeneity in MR images by using a prospective or retrospective method.

When a plurality of medical images to be registered are CT images, the image processor 720 may perform iterative reconstruction or filtering in an image domain to correct inhomogeneity in image quality due to a difference in a reconstruction filter or scan set up. Furthermore, in order to correct inhomogeneity caused by differences in inter-slice spacing and position and thickness of a slice, the image processor 720 may perform again reconstruction similar to a process of generating the slice.

The image processor 720 may correct image inhomogeneity between the plurality of medical images in order to perform registration and comparison more accurately. The image processor 720 may also perform subsequent target extraction and registration on the plurality of medical images that have undergone image inhomogeneity correction.

At times, a registration error may occur due to an obscure bone boundary caused by a partial volume effect generated in an image having low resolution. Partial volume effect refers to blurring of an image introduced when a size of an object to be imaged is less than a resolution of the image. Thus, when an object or region smaller than a resolution of an image is imaged, the object or region is not accurately represented, and thus, it may difficult to analyze a portion corresponding to the imaged object or region. In order to prevent an error in an image due to this partial volume effect, the image processor 720 may clarify a bone boundary by performing a partial volume correction method. The image processor 720 may, therefore, perform a partial volume correction method on each of the plurality of medical images to be registered.

Furthermore, the image processor 720 may also perform a partial volume correction method on an image obtained by registering the plurality of medical images and/or on diagnostic images.

The image processor 720 may extract at least one target from each of the plurality of medical images that have undergone image inhomogeneity correction to obtain a plurality of target-extracted images corresponding to a plurality of time points (operation 1020). The image processor 720 may extract a specific target via a thresholding method. The thresholding method is an image processing technique for detecting a specific target. According to the thresholding method, if a signal value (brightness or intensity value) of a region in an image is greater than or equal to a predetermined threshold, the region is detected, and if it is less than the predetermined threshold, the region is not detected. For example, in a CT image, a bone having a high HU value may appear bright. Thus, the image processor 720 may segment a bone that is a target from a medical image by setting a HU value of the bone as a threshold to detect a region having a HU value greater than or equal to the threshold.

Furthermore, the image processor 720 may segment a bone from a medical image and perform subsequent morphology on the resulting medical image to smoothly connect a boundary forming the bone. In detail, the image processor 720 may connect a disconnected portion of a boundary in an image obtained by segmenting a bone to form a closed curve so as to smoothly connect the boundary forming the bone, and fill the inside of the closed curve, thereby allowing accurate representation of the bone in the object.

Thus, the image processor 720 may extract the bone that is a target from the medical image and obtain an image of the bone that is a target-extracted image representing the target in an object. In this manner, the image processor 720 may obtain a first and a second target-extracted images respectively corresponding to first and second time points.

Before registering the target-extracted images, the image processor 720 may perform pre-processing on the target-extracted images (operation 1031) to increase accuracy of registration (operation 1032). In detail, the image processor 720 may increase a signal-to-noise ratio (SNR) in a target-extracted image by using a filter that processes an input image and attenuates noise. For example, the image processor 720 may perform Gaussian filtering or median filtering on an input image to process the input image.

Operations 1031, 1032, 1041, 1042, 1045, and 1050 will be discussed with respect to FIGS. 11 and 12. Pre-processing of a target-extracted image (operation 1031) will now be described in more detail with reference to FIG. 11.

Figure 11:
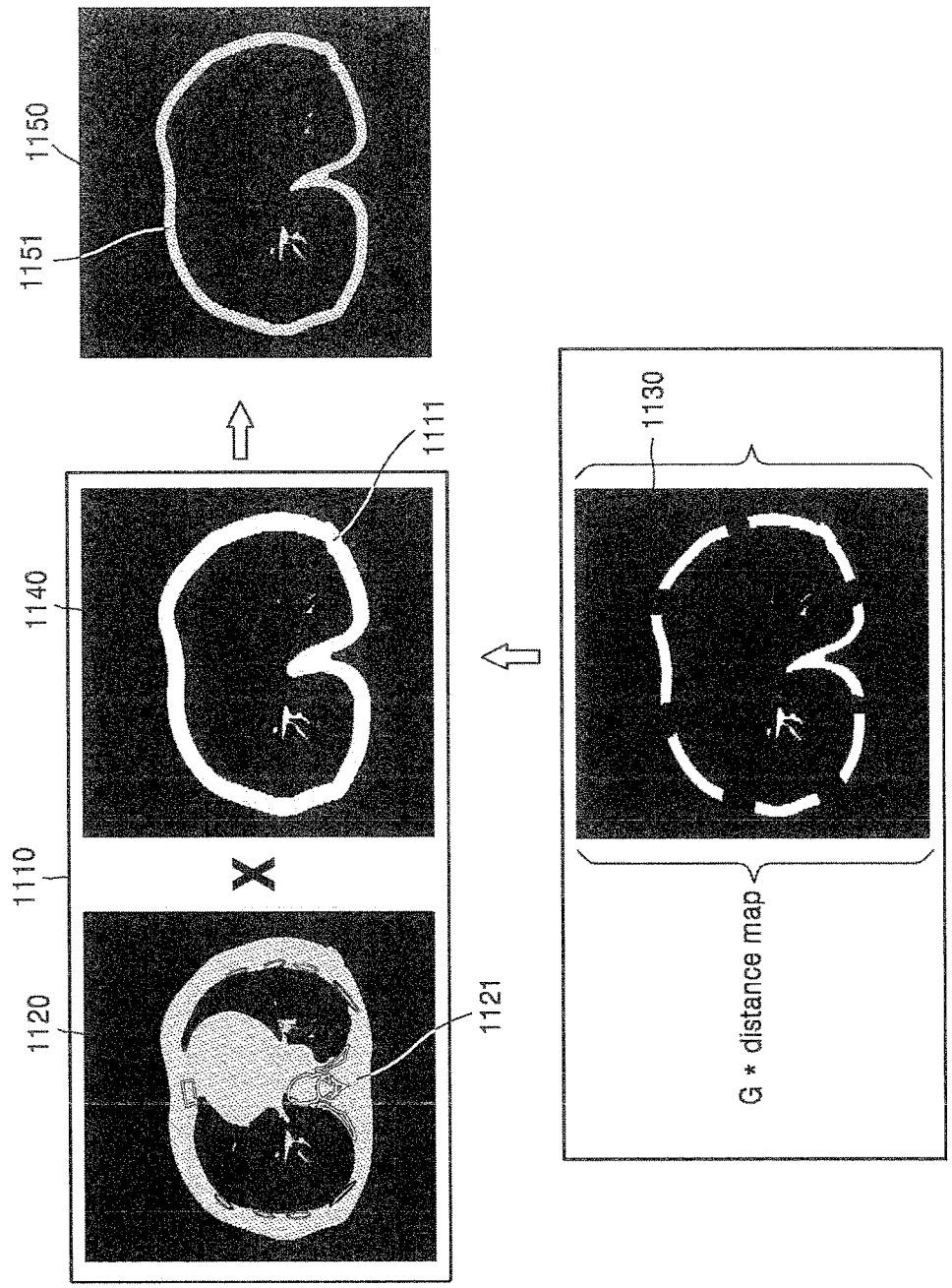
FIG. 11 is a diagram for explaining an operation of extracting a target via a medical image processing apparatus, according to an exemplary embodiment.

FIG. 11 is a diagram for explaining an operation of extracting a target via the medical image processing apparatus 700, according to an exemplary embodiment. FIG. 11 shows an example where a target-extracted image is obtained by extracting a bone from a first medical image acquired at a first time point. Furthermore, it is assumed that the first medical image is a CT image showing a cross-section of a chest.

Referring to FIG. 11, the image processor 720 may perform operation 1020 to extract a target from a first medical image 1120 and obtain a target-extracted image 1130. The target-extracted image 1130 may be a binary image obtained using the thresholding method. A signal value in a binary image is 0 or 1. Thus, in the target-extracted image 1130, a bone may have a value of 1, and the remaining portion other than the bone may have a value of 0.

The image processor 720 may then perform pre-processing (operation 1031) as described below. The image processor 720 may apply a distance map to the target-extracted image 1130 having a form of a binary image and apply a Gaussian filter G to the target-extracted image 1130 to which the distance map has been applied, thereby generating a filtered target-extracted image 1140. A distance map refers to an image processing technique that is characterized by a decrease in signal intensity away from a center of a bone, which is used as a reference point. Thus, in the filtered target-extracted image 1140, since intensity decreases as distance from the center of the bone increases, a boundary is smoothly shown.

The image processor 720 may combine the filtered target-extracted image 1140 and the first medical image 1120 together to make a signal intensity of a bone 1111 in the filtered target-extracted image 1140 similar to a signal intensity of a bone 1121 in the first medical image 1120, as shown in FIG. 11. Accordingly, in a final target-extracted image 1150, a bone 1151 is extracted from an object, and a signal intensity of the bone 1151 is depicted as being similar to that of the bone 1121 in the first medical image 1120. As described with reference to FIG. 11, the image processor 720 may extract a bone that is a target from the first medical image 1120 more accurately by using a Gaussian filter and a multiplication arithmetic operation 1110. The final target-extracted image 1150 described with reference to FIG. 11 is hereinafter referred to as a "final target-extracted image."

The image processor 720 may register target-extracted images corresponding to various time points to obtain a plurality of target-registered images. In detail, the image processor 720 may generate the target-registered images by registering the final target-extracted images (e.g., the final target-extracted image 1150) corresponding to a plurality of time points. Image registration (operation 1032) performed by the image processor 720 will now be described in more detail with reference to FIG. 12.

Figure 12:
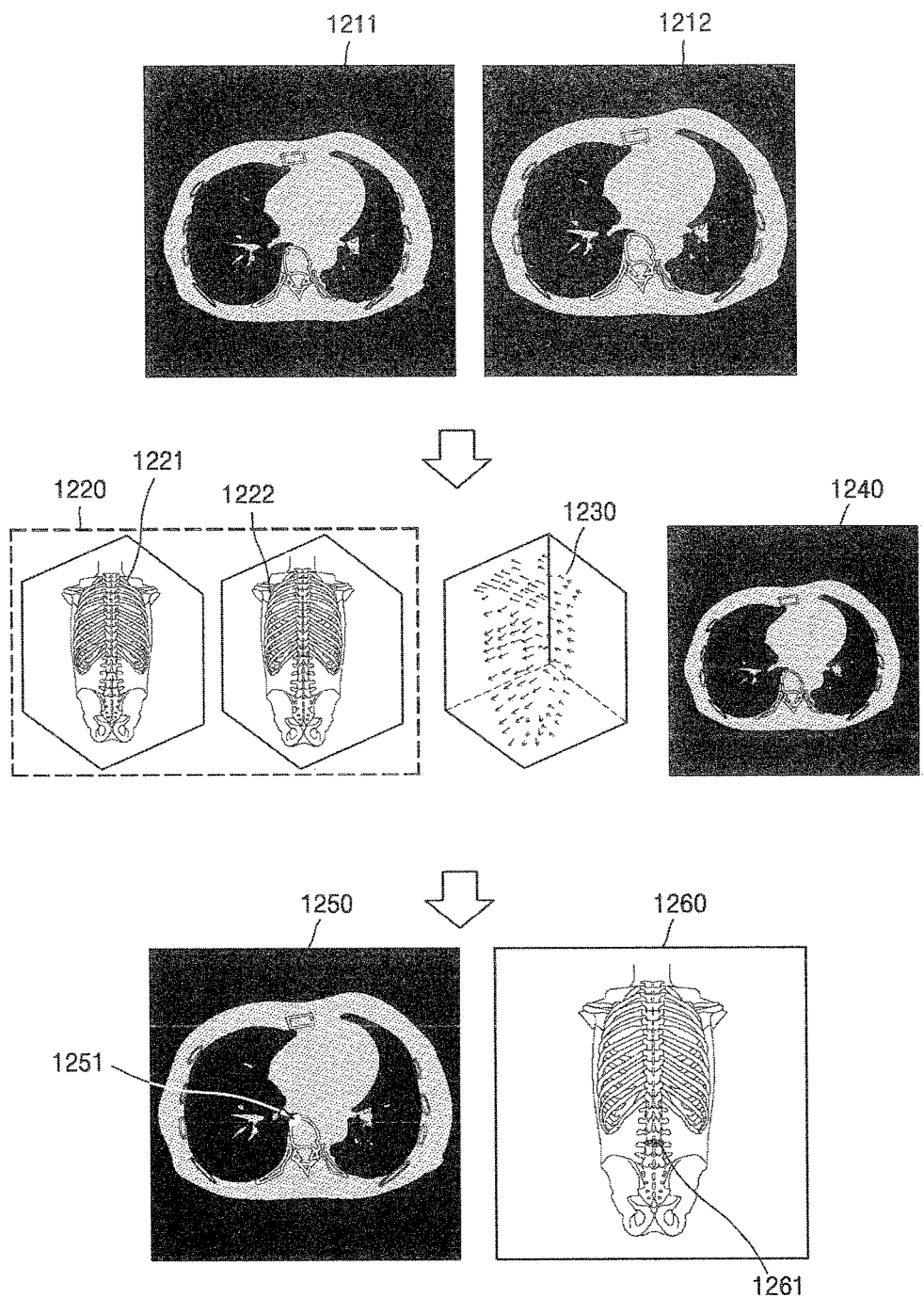
FIG. 12 is a diagram for explaining registration that is performed by a medical image processing apparatus according to an exemplary embodiment.

FIG. 12 is a diagram for explaining registration that is performed by the medical image processing apparatus 700 according to an exemplary embodiment.

To determine the degree of change in a target included in an object, the image processor 720 may generate a plurality of target-registered images by registering a plurality of target-extracted images in operation 1032. The image processor 720 may also generate the target-registered images by registering medical images. However, when medical images are registered, the image processor 720 may determine the degrees of change in the target as well as in other portions of the object depicted in the images. FIG. 12 illustrates registration for the first and second medical images 1211 and 1212.

Referring to FIG. 12, the image processor 720 may extract targets from the first and second medical images 1211 and 1212 to obtain first and second final target-extracted images 1221 and 1222, respectively. FIG. 12 illustrates an example where a final target-extracted image is obtained by extracting a target that is a bone from a CT image showing a chest of a patient that is an object. Furthermore, in the example, the first and second medical images 1211 and 1212 are 2D CT images depicting a vertical cross-section of the chest, and the first and second final target-extracted images 1221 and 1222 are 3D CT images showing bones in the chest.

The image processor 720 then performs image registration on the first and second final target-extracted images 1221 and 1222 to obtain registered images. In this case, image registration is the process of matching the remaining ones of a plurality of images to one reference image, or normalizing images to the reference image. For example, the image processor 720 may normalize the second final target-extracted image to the first final target-extracted image 1221 to increase similarity between the first and second final target-extracted images 1221 and 1222.

In detail, the image processor 720 may register the first and second final target-extracted images 1221 and 1222 by using various image registration methods. For image registration, at least one of rigid registration and non-rigid registration may be used.

Rigid registration is an algorithm for matching motion such as rotation and translation of an object or target. For example, the image processor 720 may set at least one landmark in a target bone in each of the first and second final target-extracted images 1221 and 1222 and transform the first and/or the second final target-extracted images 1221 and 1222 to decrease a distance between corresponding landmarks in the first and second final target-extracted images 1221 and 1222. In detail, the image processor 720 obtains a rotation and translation matrix that minimizes the distance between corresponding landmarks in the first and second final target-extracted images 1221 and 1222 and registers the first and second final target-extracted images 1221 and 1222 together by using the obtained rotation and translation matrix. As another example, the image processor 720 may obtain a rotation and translation matrix based on a pixel intensity similarity between landmarks in the first and second final target-extracted images 1221 and 1222 and register the first and second final target-extracted images 1221 and 1222 together by using the obtained rotation and translation matrix. In this case, the pixel intensity similarity may be a sum of square differences (SSD) value. As another example, the pixel intensity similarity may be a sum of absolute differences (SAD) value, a mean of absolute differences (MAD) value, a signal to noise ratio (SNR) value, a mean square error (MSE) value, a peak signal to noise ratio (PSNR) value, or a root mean square error (RMSE) value.

Accordingly, the image processor 720 may warp the second final target-extracted image 1222 to align with the first final target-extracted image 1221 by using the rotation and translation matrix. Furthermore, the image processor 720 may warp the first final target-extracted image 1221 to align with the second final target-extracted image 1222 by using the rotation and translation matrix. In this case, warping means adjusting an object in an image to fit a predicted state of the object by expanding, contracting and translating the object, and/or changing a state of the object such as its shape.

The image processor 720 may also perform symmetric registration to reduce a quantification error caused by blurring that may occur during warping. Symmetric registration involves warping each of the first and second final target-extracted images 1221 and 1222 and registering warped versions of the first and second final target-extracted images 1221 and 1222 to each other. In detail, the image processor 720 may perform symmetric registration to reduce a quantification error caused by blurring that may occur during warping using at least one of rigid registration and non-rigid registration.

By performing the above-described rigid registration, the image processor 720 may register at least one of overall position, size, and shape of at least one target in the first and second final target-extracted images 1221 and 1222.

Non-rigid registration is an algorithm for matching states between non-rigid objects. For example, the image processor 720 may perform non-rigid registration between the first and second final target-extracted images 1221 and 1222 by using a pixel or voxel based demons algorithm.

The image processor 720 may compute an optimal motion vector between corresponding pixels in the first and second final target-extracted images 1221 and 1222 on an image grid representing images. The image processor 720 then sets a plurality of control points in each of the first and second final target-extracted images 1221 and 1222 and computes an optimal motion vector between corresponding control points. In this case, the corresponding pixels in the first and second final target-extracted images 1221 and 1222 may be extracted based on intensity similarity.

Referring to FIG. 12, the image processor 720 may perform registration (operation 1032) by acquiring a motion vector field describing a difference between the first and second final target-extracted images 1221 and 1222 on a 3D image grid 1230 corresponding to the first and second final target-extracted images 1221 and 1222. Based on the acquired motion vector field, image processor 720 may register the first and second final target-extracted images 1221 and 1222 together by warping at least one of the first and second final target-extracted images 1221 and 1222. Since the warping of at least one of the first and second final target-extracted images 1221 and 1222 is performed in the same manner as the warping described for the rigid registration, a detailed description will be omitted.

The image processor 720 may perform image registration by using a kernel-based method such as B-spline or thin plate splines. According to the kernel-based method, landmarks are set at uniform or non-uniform intervals, and image registration is performed by adjusting motion of a landmark based on an intensity similarity between the set landmarks and adjusting motion of neighboring pixels according to a predetermined kernel.

To increase the accuracy level of image registration, the image processor 720 may roughly register a target/object by initially performing rigid registration and then register the target/object again by further performing non-rigid registration.

The image processor 720 may obtain first and second target-registered images (not shown) by registering the first and second final target-extracted images 1221 and 1222 according to the above-described registration methods. Referring to FIG. 12, an image 1240 is obtained by overlaying the first and second target-registered images, and a variation between the first and second target-registered images may be measured by comparing the first and second target-registered images with each other (operation 1041). For example, the image processor 720 may quantify the degree of change in a target based on a variation in pixel intensity among a plurality of registered images.

In this case, the variation may be measured on a pixel-by-pixel basis. In detail, the image processor 720 may compare corresponding pixels in the first and second target-registered images and calculate a variation for each pixel. For example, if corresponding pixels in the first and second target-registered images respectively have first and second pixel values, a variation may be the second pixel value minus the first pixel value. Accordingly, in a CT image, if a variation is 0, it means that no change has occurred in a target bone. If a variation has a positive (+) value, it means that a blastic metastatic cancer capable of forming a bone is progressing, and if a variation has a negative (−) value, it means that a lytic metastatic cancer capable of destroying a bone is progressing. The degree of progression of bone cancer may be determined based on a value of a variation. For example, a variation may have a large absolute value when a bone cancer is progressing quickly and have a small absolute value when the bone cancer is progressing slowly.

The image processor 720 may classify the degree of change into, for example, three stages based on a variation in pixel intensity. The three stages may be the no change stage, the target formation stage, and the target destruction stage. Target formation stage and the target destruction stage may be further subdivided into substages depending on the variation value.

In a CT image, bone, muscle tissue, and water may have values of about 350 HU, about 40 HU, and 0 HU, respectively. Furthermore, fat may have a value in a range of between about −80 HU and about −120 HU, and a tumor may have a value greater than or equal to 10 HU. Thus, based on a pixel difference (variation) between two images, the extent to which bone has been formed or destroyed may be determined.

Furthermore, the image processor 720 may perform post-processing (operation 1042) to increase accuracy in extracting a portion where a change has occurred in a target based on a value of a variation. Accordingly, after calculating a variation, the image processor 720 may perform filtering for removing a target determined as a false positive before generating a diagnostic image. In other words, when a portion of the target where a change has occurred between first and second target-registered images (not shown) is acquired, if the portion of the target is not determined to represent a change in status of metastatic bone cancer, that portion of the target may be removed.

For example, metastatic bone cancer may have an approximately round shape. Thus, if a portion of a target where a change has occurred between the first and second target-registered images has a linear or elongated shape instead of a round shape, the change may not be determined as a change in status of the metastatic bone cancer. Thus, the image processor 720 may remove the portion of the target having an elongated shape via structure filtering such as Gabor filtering.

When accurate registration is not performed during image registration, a bone in a first target-extracted image may not accurately match its corresponding bone in a second target-extracted image. In this case, due to a mismatch between the corresponding bones, it may be determined that there is a changed portion of the target having an elongated shape. Thus, for a given target, when the changed portion of the target has a predetermined shape (elongated shape, etc.), the image processor 720 may remove the changed portion of the target. The predetermined shape may be determined experimentally or clinically.

The image processor 720 may acquire a confidence level for quantified values of voxels, and reflect the acquired confidence level as a weight in a change in status of metastatic bone cancer. In this case, the voxels may be in the first and second target-registered images. The voxels may also be in the first and second target-extracted images.

A quantified value of a voxel at which a Jacobian determinant that may be computed as a registration vector based on nearly-incompressibility of a bone has a value not close to 1 has a low confidence level. If the confidence level is low, a weight that decreases in proportion to the confidence level may be applied to a change in status of a metastatic bone cancer.

In detail, water that constitutes 60% or more of components of tissues in a human body generally does not compress or expand at body temperature. Nearly-incompressibility is a property similar to incompressibility. A bone matter has nearly-incompressibility, and a Jacobian determinant may be calculated based on the nearly-incompressibility. A confidence level for a quantified value of a voxel may be computed according to the calculated Jacobian determinant.

Furthermore, to suppress occurrences of false positives in a registered image, low difference value suppression, cartilage exclusion, scapular suppression, Gaussian smoothing, etc. may be performed during post-processing of registered images (operation 1042).

Low difference value suppression may be performed to suppress portions having a low difference value in registered images. Furthermore, when registration is performed around a chest, movements of the chest and scapula may be different, and due to such a difference, a registration error in the scapula may increase. Thus, the image processor 720 may perform scapular suppression to reduce quantification error that occurs in the scapula.

Additionally, noise such as image spikes may be contained in portions in registered images that show change in bone matter. In this case, Gaussian smoothing may be performed to suppress such noise.

The image processor 720 may generate a diagnostic image that indicates a plurality of stages quantified according to the variation in such a manner as to distinguish them from one another. That is, the image processor 720 may distinguish portions where a target has not changed, has been newly formed, and has been destroyed. Furthermore, the image processor 720 may subdivide the portion where the target has been formed into a plurality of stages according to a value of variation and indicate the plurality of stages. For example, the portion where the target has new formations may be subdivided into stages when a variation in HU value is in a range that is greater than 0 and less than or equal to 50, in a range that is greater than 50 and less than or equal to 100, and in a range that is greater than 100, etc. The image processor 720 may also subdivide the portion where the target has new destructions into a plurality of stages according to a value of variation and indicate the plurality of stages. For example, the portion where the target has been destroyed may be subdivided into stages when a variation in HU value is greater than −50 and less than or equal to 0, is greater than −100 and less than or equal to −50, and is less than or equal to −100, etc.

Furthermore, when a representation scale for change can be further subdivided into smaller parts, the degree of change may be represented as having continuous values without being divided into a plurality of stages. As the number of stages increases, the plurality of stages may not be clearly distinguished from one another and appear to have continuous values. For example, if color is used to represent degree of change, as more colors are used, the colors may blend into each other.

The image processor 720 may map the plurality of stages to at least one of different colors, different shapes, and different lines (operation 1045). Furthermore, the user interface unit 740 may receive input to use one of colors (including grayscale), shapes, and lines for the mapping. The image processor 720 may then obtain a diagnostic image based on the mapping (operation 1050).

For example, the plurality of stages may include seven (7) stages: (i) when no change occurs in a target, (ii) when a variation in HU value is greater than 0 and less than or equal to 50, iii) when the variation in HU value is greater than 50 and less than or equal to 100, iv) when the variation in HU value is greater than 100, v) when the variation in HU value is greater than −50 and less than or equal to 0, vi) when the variation in HU value is greater than −100 and less than or equal to −50, and vii) when the variation in HU value is less than or equal to −100. It is also assumed that a color scale has seven grades, for example, red, orange, yellow, green, blue, indigo, and violet.

In this case, the stages (i) through (vii) may be mapped to green, yellow, orange, red, blue, indigo, and violet colors, respectively. The image processor 720 may also indicate changed portions in a diagnostic image by using colors mapped thereto in such a manner that the plurality of stages are distinguished from one another, thereby generating diagnostic images 1250 and 1260.

Furthermore, when the plurality of stages are respectively mapped to a plurality of colors, the user interface unit 740 may receive a user input for selecting colors to correspond to the plurality of stages.

Referring to FIG. 12, the image processor 720 generates the diagnostic images 1250 and 1260 by using the mapping described above. Since a target is formed near a vertebra, the diagnostic image 1250 includes a mark 1251 indicating a position where the target has been newly formed. The diagnostic image 1260 also includes a similar mark 1261 indicating a position where the target has been newly formed.

In this case, the diagnostic image 1250 (and 1260) may be obtained by classifying a variation acquired by comparing target-registered images into a plurality of stages and indicating the plurality of stages on one of a plurality of medical images.

Blending for generating a diagnostic image will now be described in detail with reference to FIG. 13.

Figure 13:
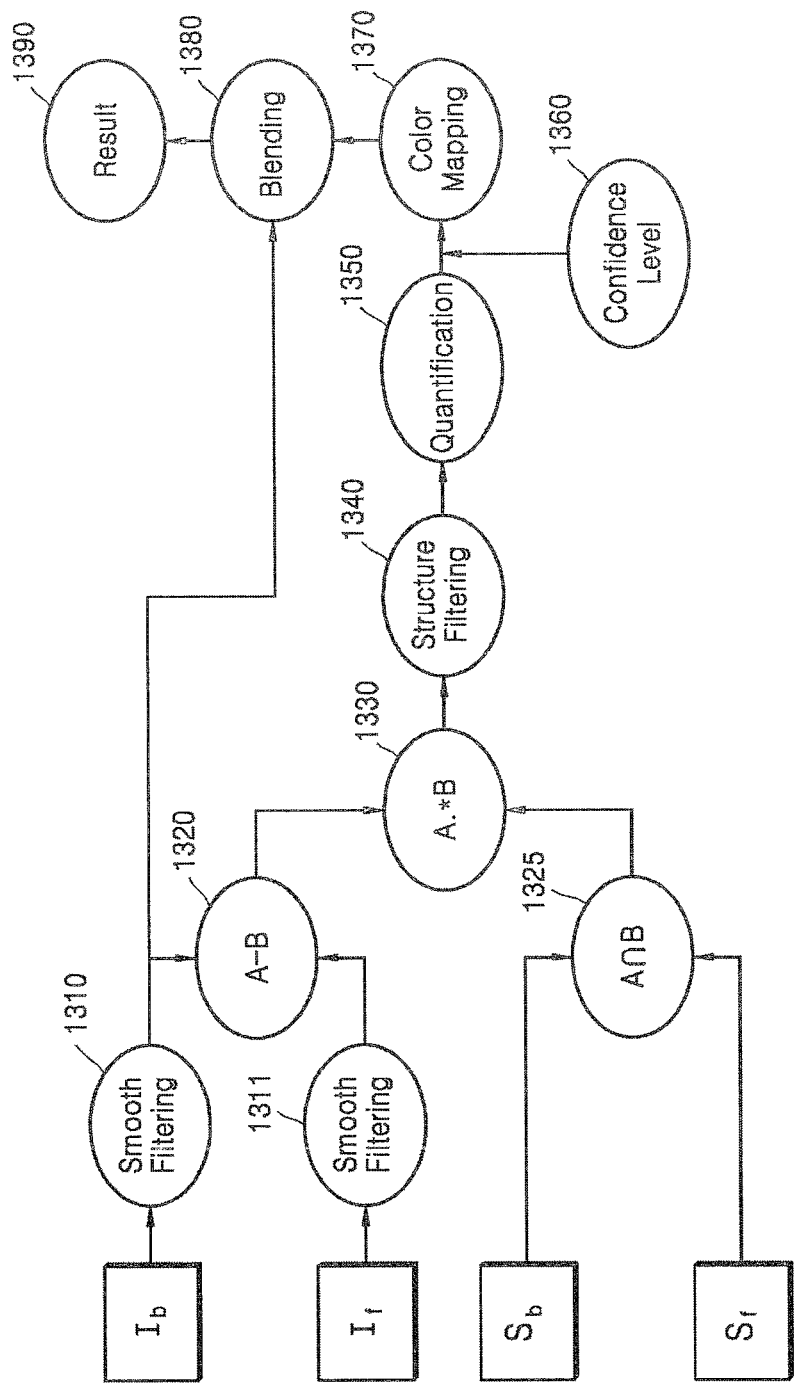
FIG. 13 is a diagram for explaining a blending operation that is performed by a medical image processing apparatus according to an exemplary embodiment.

FIG. 13 is a diagram for explaining a blending operation that is performed by the medical image processing apparatus 700 according to an exemplary embodiment.

Referring to FIG. 13, $I_b$ represents a first registered image obtained from a first medical image at a first time point, and $I_f$ represents a second registered image obtained from a second medical image at a second time point. $S_b$ and $S_f$ respectively represent first and second target-extracted images based on the first and second registered images.

After registration, the image processor 720 may perform filtering on each of the first and second registered images $I_b$ and $I_f$. In detail, the image processor 720 may perform smooth filtering operations 1310 and 1311 to define surfaces or edges of an object in the first and second registered images $I_b$ and $I_f$, respectively. The image processor 720 then obtains a difference image between the first and second registered images $I_b$ and $I_f$. The image processor 720 also generates, based on an image generated by intersection operation 1325 between the first and second target-extracted images $S_b$ and $S_f$, an image showing only a difference between targets in the first and second registered images $I_b$ and $I_f$ or a changed portion of a target. The image processor 720 then performs a combination operation 1330 on the image generated by difference operation 1320 and the image generated by intersection operation 1325 to generate an image that indicates a change in the target.

Accordingly, in FIG. 13, the first registered image $I_b$ may be a baseline CT image and the second registered image $I_f$ may be a follow-up CT image. The first target-extracted image $S_b$ may be a binary mask image obtained by extracting only a bone area from the baseline CT image (first registered image $I_b$) and the second target-extracted image $S_f$ may be a binary mask image obtained by extracting only a bone area from the follow-up CT image (second registered image $I_f$). 'A' is a differential image after registration, whereas 'B' is a bone area binary mask after registration. Therefore, combination operation 1330 expressed by "A.*B" may be an image displaying only a bone area from the differential image after registration.

The image processor 720 may accurately extract a portion of the target that has changed by performing post-processing (e. g, operation 1042 in FIG. 10) such as structure filtering on the image generated by combination operation 1330. Then, the image processor 720 quantifies the degree of change in the target in an image 1340 that has undergone the structure filtering, performs color mapping on the quantified degree of change 1350, and generates an image 1370 showing the changed portion of target via the color mapping. Finally, the image processor 720 may generate a diagnostic image 1390 by blending the image 1370 with the first registered image $I_b$.

The diagnostic image 1390 will now be described in more detail with reference to FIG. 14.

Figure 14:
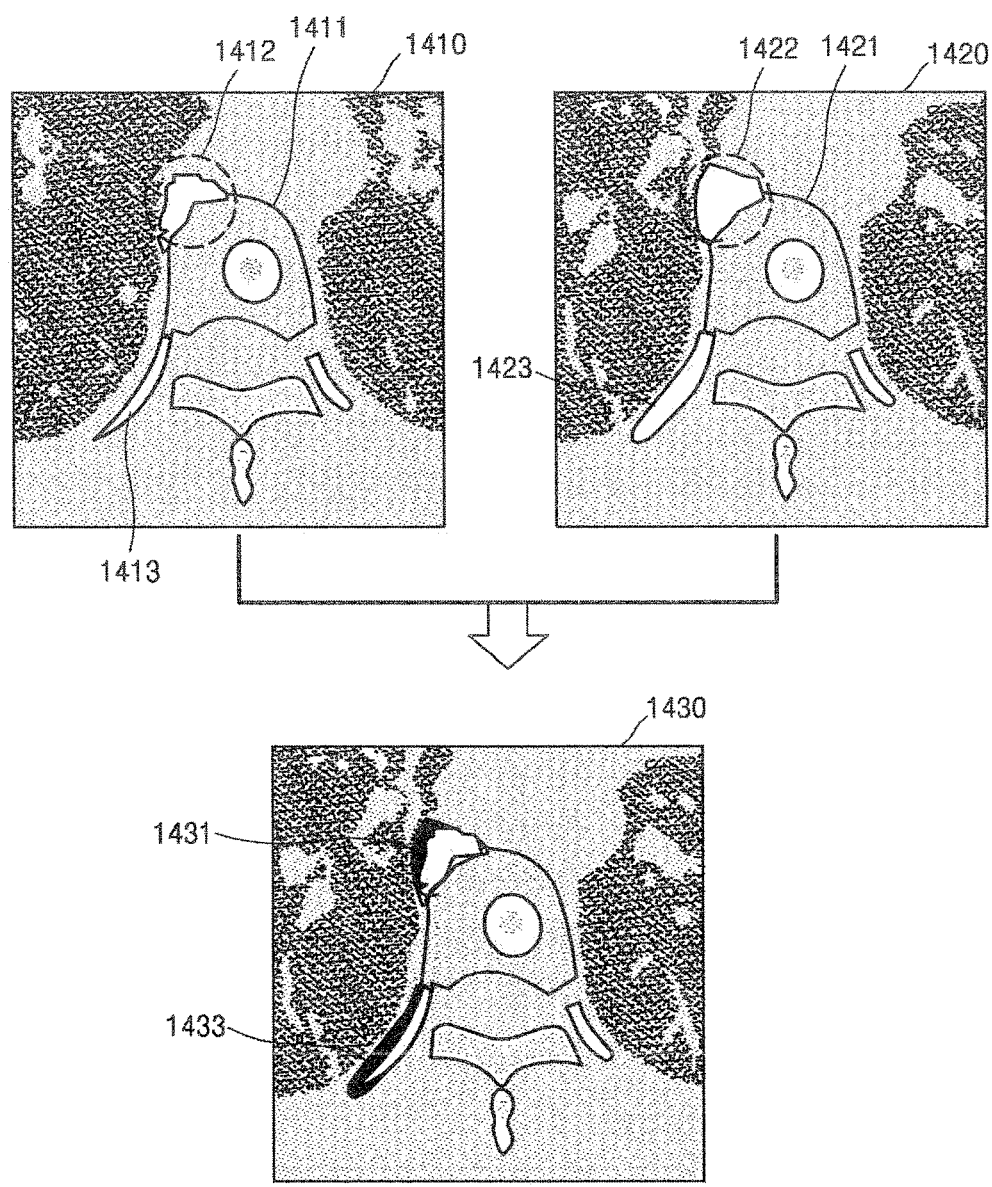
FIG. 14 is a diagram for explaining a diagnostic image acquired by a medical image processing apparatus, according to an exemplary embodiment.

FIG. 14 is a diagram for explaining a diagnostic image obtained by the medical image processing apparatus 700, according to an exemplary embodiment.

FIG. 14 shows first medical image 1410 and second medical image 1420 obtained by performing CT scans on vertebrae 1411 and 1421 at first and second time points, respectively.

As seen on the first medical image 1410, a metastatic bone cancer 1412 has occurred in a portion of vertebra 1411. As seen on the second medical image 1420, a metastatic bone cancer 1422 has occurred in a portion of vertebra 1421. By comparing the first medical image 1410 and second medical image 1420 with each other, it can be seen that the metastatic bone cancer 1422 has become worse than the metastatic bone cancer 1412, as indicated by the size of the metastatic bone cancer 1422 compared to the metastatic bone cancer 1412.

The image processor 720 may quantify a variation between the metastatic bone cancers 1412 and 1422 to generate a diagnostic image 1430 that indicates the degree of change in the vertebra 1411 via the mapping described with reference to the operation 1045 in FIG. 10.

If the variation between the metastatic bone cancers 1412 and 1422 in terms of a HU value of a CT image is in stage (iv) when the variation in HU value is greater than 100, the image processor 720 may indicate the variation by using a color (e.g., red) mapped to stage (iv).

Furthermore, the mismatch may occur between a bone 1413 in the first medical image 1410 and a bone 1423 in the second medical image 1420. Since a mismatched portion 1433 does not represent a changed portion of the target but exists due to inaccurate registration, the mismatched portion 1433 may be removed via structure filtering.

The image processor 720 may perform mapping on the plurality of stages into which the degree of change is classified by using a color scale or grayscale, according to linear transform, Gamma transform, or contrast stretching transformation. The user interface unit 740 may also receive user input for selecting a transformation technique to be used for the mapping by the image processor 720.

Figure 15:
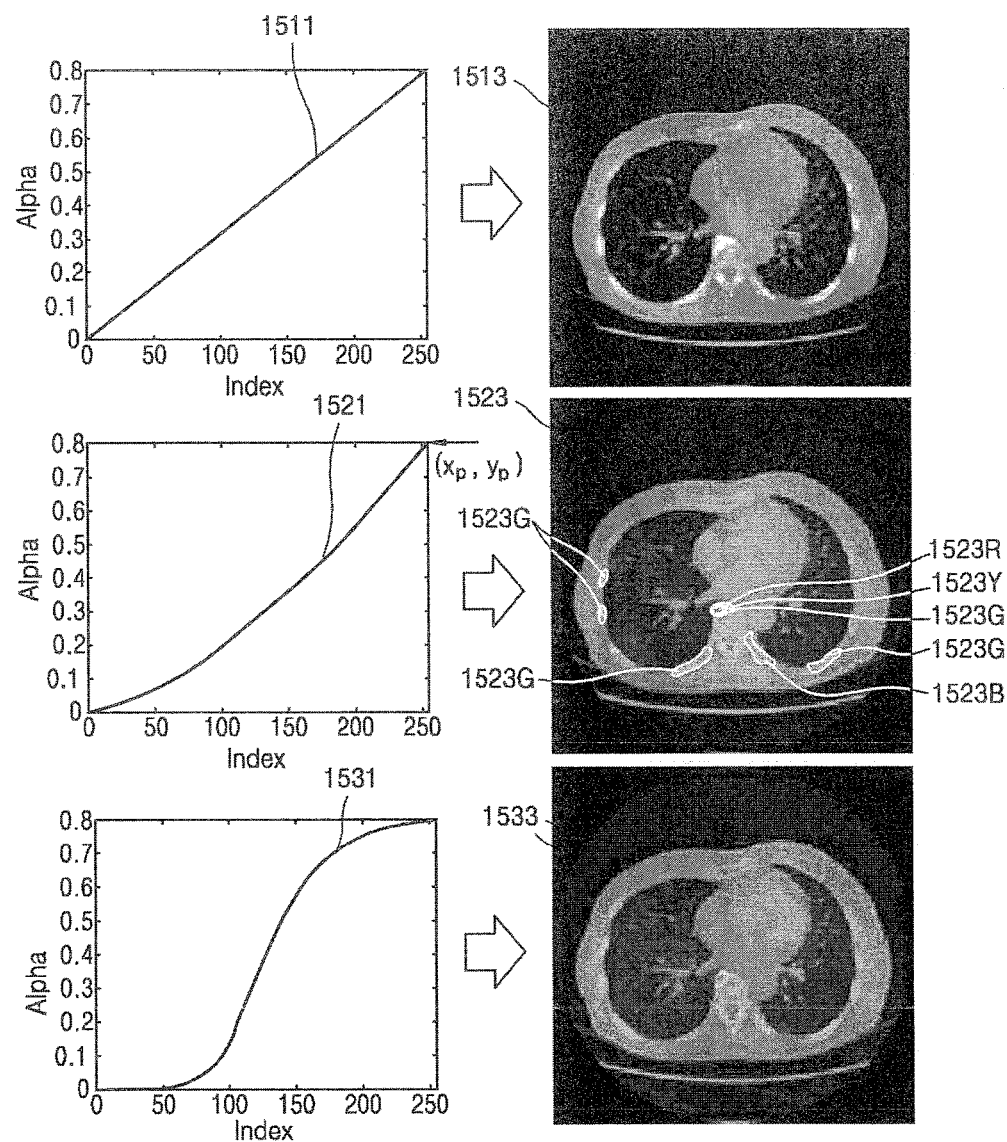
FIG. 15 is a diagram for explaining a blending operation that is performed by a medical image processing apparatus according to an exemplary embodiment.

FIG. 15 is a diagram for explaining a blending operation that is performed by the medical image processing apparatus 700 according to an exemplary embodiment Referring to FIG. 15, graphs 1511 and 1521 respectively represent linear transform and Gamma transform, and graph 1531 represents contrast stretching transformation. In the graphs 1511, 1521, and 1531, the abscissa (x-axis) denotes an index corresponding to a variation in signal intensity indicating the degree of change in a target, and the ordinate (y-axis) denotes opacity or an index for each color in a color scale.

The image processor 720 may generate a diagnostic image by blending an original medical image with an image obtained by mapping a plurality of stages to a color scale or grayscale, and in particular, with an image showing the degree of change in at least one target, using linear transformation, Gamma transformation, or contrast stretching transformation. Accordingly, the image processor 720 may perform blending operations using linear transformation, Gamma transformation, or contrast stretching transformation to respectively generate diagnostic images 1513, 1523, and 1533.

Referring to the diagnostic image 1523, a red portion 1523R represents bone formation, a green portion 1523G represents no change in a bone, and a blue portion 1523B represents bone destruction. Furthermore, a yellow portion 1523Y surrounding the red portion 1523R represents a portion where a smaller amount of bone is formed than in the red portion 1523R. In other words, bone density in the yellow portion 1523Y is lower than that in the red portion 1523R. Thus, the user may easily identify the degree of change in a target and quickly determine the degrees of change in a quantified plurality of stages via the diagnostic image 1523. The user may quickly determine the degree of progression of a lytic metastatic cancer and a blastic metastatic cancer via the diagnostic image 1523.

Figure 16:
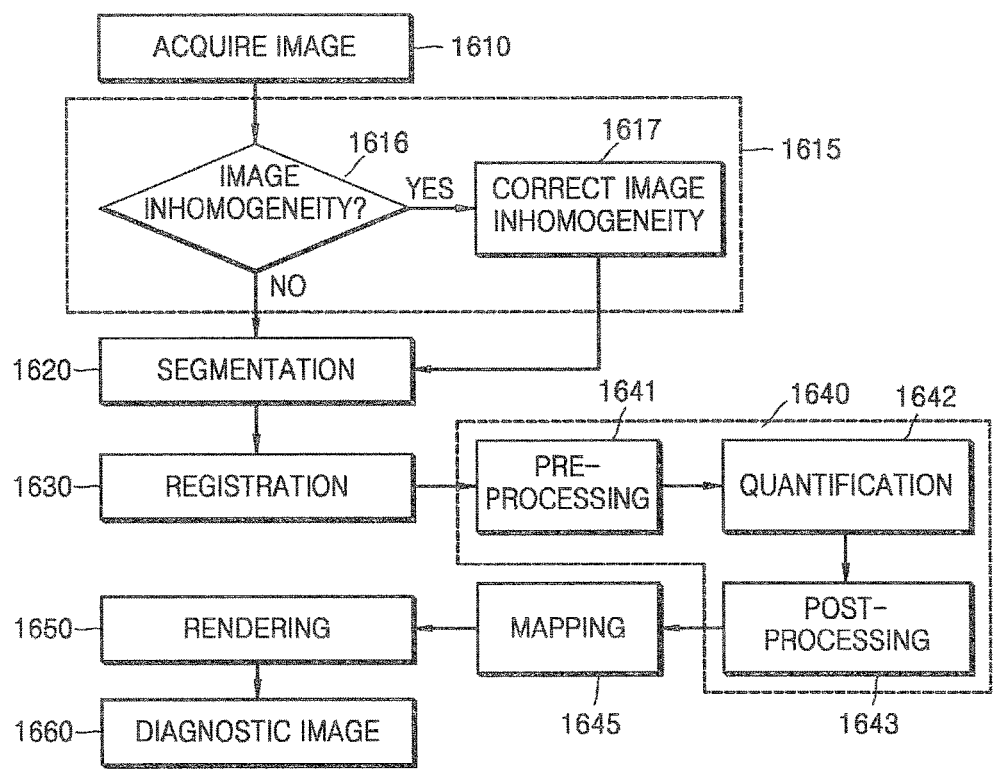
FIG. 16 is a flowchart for explaining an operation of a medical image processing apparatus, according to an exemplary embodiment.

FIG. 16 is a flowchart for explaining an operation of the medical image processing apparatus 700 according to an exemplary embodiment. Since operations 1610, 1615, 1620, 1630, 1640, 1645, and 1660 in FIG. 16 correspond to operations 1010, 1015, 1020, 1030, 1040, 1045, and 1050, respectively, described with reference to FIG. 10, descriptions already provided with reference to FIG. 10 will be omitted below.

Furthermore, since a rendering operation (operation 1650) corresponds to blending operation 1380 described with reference to FIG. 13, descriptions already provided with reference to FIG. 13 will be omitted below.

Referring to FIG. 16, the image processor 720 acquires a plurality of medical images (operation 1610).

The image processor 720 then determines whether image inhomogeneity is present in the acquired medical images (operation 1616). If the image inhomogeneity is present, the image processor 720 corrects the image inhomogeneity (operation 1617). If the image inhomogeneity is not present, the image processor 720 performs target extraction (operation 1620).

The image processor 720 extracts at least one target from each of the medical images to obtain a plurality of target-extracted images corresponding to a plurality of time points (operation 1620).

The image processor 720 then obtains target-registered images by registering the target-extracted images (operation 1630). The image processor 720 may perform pre-processing to increase accuracy in calculating a variation between the target-registered images (operation 1641). Since operation 1641 corresponds to the pre-processing (operation 1031), a detailed description thereof will be omitted below. The preprocessing (operation 1031) is followed by quantification (operation 1642) and post-processing (operation 1643). Since quantification (operation 1642) and post-processing (operation 1643) respectively correspond to operations 1041 and 1042 described with reference to FIG. 10, detailed descriptions will be omitted below.

The image processor 720 then maps the plurality of stages to at least one of different colors, different shapes, and different lines (operation 1645), renders an image indicating the plurality of stages that have undergone color mapping on at least one of the plurality of medical images (operation 1650), and generates a diagnostic image (operation 1660).

Figure 17:
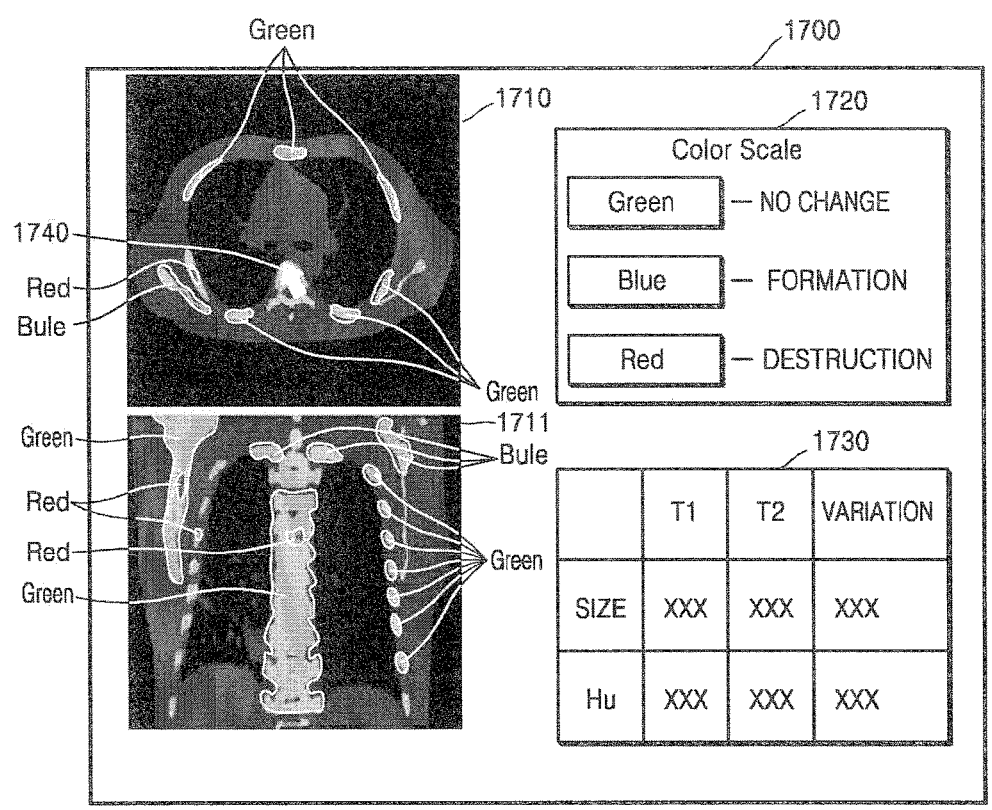
FIG. 17 illustrates a user interface screen output from a medical image processing apparatus, according to an exemplary embodiment.

FIG. 17 illustrates a user interface screen output from the medical image processing apparatus 700, according to an exemplary embodiment.

The display unit 730 may display a screen 1700 including diagnostic images 1710 and 1711. The image processor 720 may calculate the degree of change in at least one target, and the display unit 730 may display the screen 1700 including information 1730 with numeric results. Thus, the display unit 730 may display the screen 1700 including the diagnostic images 1710 and 1711 along with the information 1730. In detail, when the user selects a predetermined target via the user interface unit 740, the image processor 720 may calculate the degree of change that has occurred in the selected predetermined target. Alternatively, when the user places a selection marker 1740 at a predetermined position via the user interface unit 740, numerical values corresponding to a variation in a target at the predetermined position where the selection marker 1740 is placed may be generated, and the information 1730 is displayed.

Furthermore, the display unit 730 may output the screen 1700 including information 1720 for guiding colors indicating the degree of change.

As described above, it is assumed herein that the plurality of stages may include 7 stages: (i) when no change occurs in a target, (ii) when a variation in HU value is greater than 0 and less than or equal to 50, iii) when the variation in HU value is greater than 50 and less than or equal to 100, iv) when the variation in HU value is greater than 100, v) when the variation in HU value is greater than −50 and less than or equal to 0, vi) when the variation in HU value is greater than −100 and less than or equal to −50, and vii) when the variation in HU value is less than or equal to −100. It is also assumed that a color scale uses seven colors such as, for example, red, orange, yellow, green, blue, indigo, and violet.

In this case, the stages (i) through (vii) may be mapped respectively to green, yellow, orange, red, blue, indigo, and violet colors. The image processor 720 may indicate changed portions in a diagnostic image by using colors in such a manner that the plurality of stages are distinguished from one another, thereby generating the diagnostic images 1710 and 1711

Figure 18:
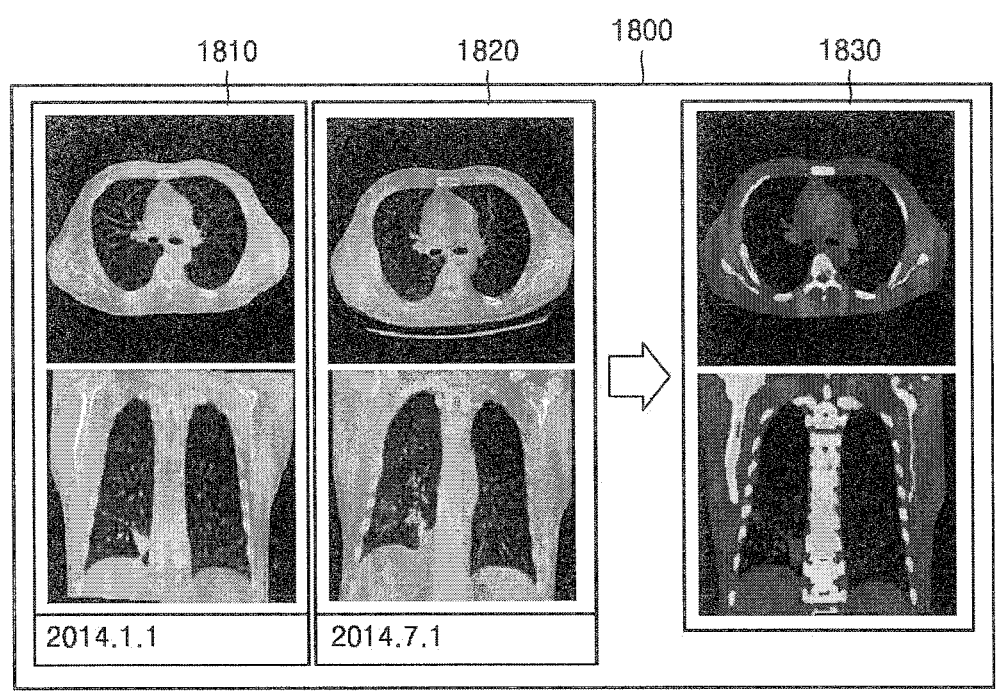
FIG. 18 illustrates a user interface screen output from a medical image processing apparatus, according to another exemplary embodiment.

FIG. 18 illustrates a user interface screen output from the medical image processing apparatus 700, according to another exemplary embodiment.

Referring to FIG. 18, the display unit 730 may display a screen 1800 including a first medical image 1810, a second medical image 1820, and a diagnostic image 1830. The diagnostic images 1710 and 1711 may correspond to the diagnostic image 1830, and, hence, generated from the first medical image 1810 and the second medical image 1820.

Figure 19:
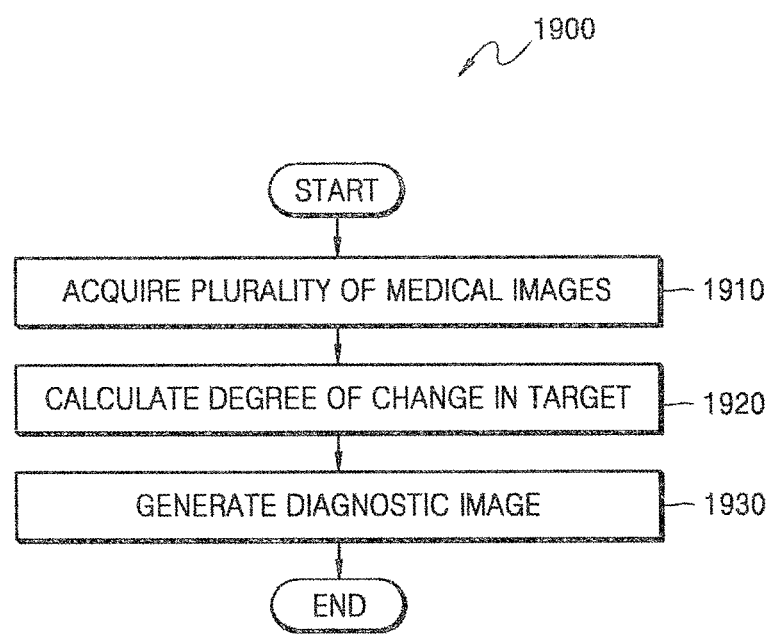
FIG. 19 is a flowchart of a medical image processing method according to an exemplary embodiment.

FIG. 19 is a flowchart of a medical image processing method 1900 according to an exemplary embodiment. The medical image processing method 1900 according to the present exemplary embodiment includes operations corresponding to the configurations of the medical image processing apparatuses 600 and 700 according to the exemplary embodiments described with reference to FIGS. 1 through 18. Thus, descriptions already provided with reference to FIGS. 1 through 18 will be omitted below. The medical image processing method 1900 will now be described with respect to the medical image processing apparatus 700 of FIG. 7.

Referring to FIG. 19, according to the medical image processing method 1900, a plurality of medical images representing an object including at least one target are acquired at a plurality of different time points (operation 1910). Operation 1910 may be performed by the data acquisition unit 710.

The degree of change in a target that has occurred during the plurality of different time points is calculated based on the acquired medical images (operation 1920) by the image processor 720.

A diagnostic image indicating the degree in change in a target calculated in operation 1920 is generated (operation 1930). In detail, operation 1930 may include classifying the degree of change that has occurred during the plurality of time points and generating a diagnostic image indicating the plurality of stages in such a manner as to distinguish the various stages. The change may include at least one of physiological change, position change, size change, and shape change that have occurred in a target.

Operation 1930 may also include generating registered medical images by registering the plurality of medical images, quantifying the degree of change as a plurality of stages based on a variation in pixel intensity between the registered medical images, and generating a diagnostic image showing the quantified stages in such a manner that they are distinguished from one another. The distinguishing may be done with, for example, colors, shapes, or lines.

As described above, in the medical image processing apparatuses and methods according to the exemplary embodiments, a diagnostic image indicating the degree of change in a target may be generated monitoring change in the target(s), thereby facilitating diagnosis of a patient.

The degree of change in a target may be quantified as a plurality of stages, and a diagnostic image indicating the plurality of stages in such a manner as to distinguish each from others may be generated, thereby allowing the user to diagnose the progression of disease.

When the target is a bone, the user may identify the degree of progression of bone cancer via a diagnostic image.

Various embodiments of the disclosure may be written as computer programs and may be implemented in general-use digital computers that execute the programs using a non-transitory computer-readable recording medium.

Non-transitory computer-readable recording medium may include, for example, magnetic storage media (e.g., ROM, floppy disks, hard disks, etc.), optical recording media (e.g., CD-ROMs, or DVDs), etc.

While various embodiments of the disclosure have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What is claimed is:

1. A medical image processing apparatus comprising:
a data acquisition unit configured to acquire a plurality of medical images representing an object, including at least one bone in the object, corresponding to a plurality of different time points, wherein at least one of the plurality of medical images correspond to one of the plurality of different time points;
an image processor configured to:
obtain a plurality of bone-extracted images respectively corresponding to the plurality of different time points by extracting the at least one bone from each of the plurality of medical images,
generate a plurality of registered images by registering the plurality of bone-extracted images,
calculate, based on variation in pixel intensity between corresponding pixels in the plurality of registered images, at least one degree of change that has occurred in the at least one bone over the plurality of different time points,
classify the at least one degree of change into one of a plurality of stages based on the variation in pixel intensity, the plurality of stages comprising: a bone formation stage if the variation has a first type value, a bone destruction stage if the variation has a second type value, and a no change stage if the variation is zero, and
generate, based on the plurality of registered images, a diagnostic image that shows the at least one degree of change in the at least one bone over the plurality of different time points; and
a display configured to display a screen including the diagnostic image, in which a portion corresponding to the no change stage in the bone, a portion corresponding to the bone formation stage, and a portion corresponding to the bone destruction stage, are respectively represented by a first color, a second color and a third color, for representing a progression of metastatic bone cancer over time including the plurality of different time points, and
wherein the first color, the second color and the third color are different from each from other.

2. The medical image processing apparatus of claim 1, wherein the image processor is configured to distinguish each of the plurality of stages from others of the plurality of stages.

3. The medical image processing apparatus of claim 1, wherein the image processor is configured to register the plurality of medical images to generate the plurality of registered images.

4. The medical image processing apparatus of claim 1, wherein the image processor is configured to distinguish each of the plurality of stages in the diagnostic image by use of at least one of shapes, marks, and lines.

5. The medical image processing apparatus of claim 4, further comprising a user interface unit configured to receive input to select the at least one of the shapes, the marks, and the lines to distinguish each of the plurality of stages.

6. The medical image processing apparatus of claim 1, wherein the at least one degree of change comprises at least one of a physiological change, a position change, a size change, and a shape change.

7. The medical image processing apparatus of claim 1, wherein the object comprises a part of a patient's body, and the at least one bone is at least one bone in the patient's body, and wherein the metastatic bone cancer comprises at least one of lytic metastatic cancer and blastic metastatic cancer.

8. The medical image processing apparatus of claim 1, wherein the diagnostic image comprises a bone-extracted image representing the at least one bone and showing the at least one degree of change as one of the plurality of stages including the no change stage, the bone formation stage and the bone destruction stage.

9. The medical image processing apparatus of claim 1, wherein the diagnostic image comprises an overlay image obtained by registering and superimposing the plurality of medical images and showing the at least one degree of change as one of the plurality of stages including the no change stage, the bone formation stage and the bone destruction stage.

10. The medical image processing apparatus of claim 1, wherein the diagnostic image comprises a blended image obtained by blending at least one of the plurality of medical images with an image showing the at least one degree of change that has been classified into one of the plurality of stages including the no change stage, the bone formation stage and the bone destruction stage.

11. The medical image processing apparatus of claim 1, wherein the image processor is configured to generate the plurality of registered images by registering the plurality of bone-extracted images using at least one of rigid registration and non-rigid registration, and wherein registering is symmetric registering.

12. The medical image processing apparatus of claim 1, wherein the image processor is configured to map the plurality of stages including the no change stage, the bone formation stage and the bone destruction stage to colors and to indicate the at least one degree of change in the at least one bone by using the mapped colors and wherein the image processor is configured to generate the diagnostic image by blending at least one of the plurality of medical images with an image showing the at least one degree of change in the at least one bone using the mapped colors, using at least one of linear transformation, Gamma transformation, or contrast stretching transformation.

13. The medical image processing apparatus of claim 1, wherein the image processor is configured to filter the plurality of registered images to remove a false positive having a predetermined form and to generate the diagnostic image based on the filtered plurality of registered images.

14. The medical image processing apparatus of claim 1, further comprising a display unit configured to display one or more of: the diagnostic image, at least one of the plurality of medical images, and at least one of the plurality of registered images.

15. The medical image processing apparatus of claim 1, wherein the image processor is configured to make a numerical calculation for the at least one degree of change in the at least one bone and to generate information indicating a result of the numerical calculation, and the medical image processing apparatus further comprising a display unit configured to display the information and the diagnostic image.

16. The medical image processing apparatus of claim 1, wherein the plurality of medical images is a plurality of computed tomography (CT) images, and the image processor is configured to perform iterative reconstruction or filtering in an image domain to correct inhomogeneity in image quality of the plurality of CT images.

17. The medical image processing apparatus of claim 1, wherein the image processor is configured to perform a partial volume correction method on at least one of the plurality of medical images and the diagnostic image.

18. A medical image processing method comprising:
acquiring a plurality of medical images representing an object, including at least one bone in the object, corresponding to a plurality of different time points, wherein at least one of the plurality of medical images correspond to one of the plurality of different time points;
obtaining a plurality of bone-extracted images respectively corresponding to the plurality of different time points by extracting the at least one bone from each of the plurality of medical images;
generating a plurality of registered images by registering the plurality of bone-extracted images;
calculating, based on variation in pixel intensity between corresponding pixels in the plurality of registered images, at least one degree of change that has occurred in the at least one bone over the plurality of different time points;
classifying the at least one degree of change into one of a plurality of stages based on the variation in pixel intensity, the plurality of stages comprising: a bone formation stage if the variation has a first type value, a bone destruction stage if the variation has a second type value, and a no change stage if the variation is zero;
generating a diagnostic image that shows the at least one degree of change in the at least one bone; and
displaying a screen including the diagnostic image, in which a portion corresponding to the no change stage in the bone, a portion corresponding to the bone formation stage, and a portion corresponding to the bone destruction stage are represented by a first color, a second color and a third color, respectively, for representing a progression of metastatic bone cancer over time including the plurality of different time points, and
wherein the first color, the second color and the third color are different from each other.

19. The medical image processing apparatus of claim 1, wherein the image processor is further configured correct image inhomogeneity for the plurality of medical images, and obtain the plurality of hone-extracted images by extracting the at least one bone from each of the inhomogeneity corrected plurality of medical images.

* * * * *